(12) United States Patent
Filipiak et al.

(10) Patent No.: US 9,820,841 B2
(45) Date of Patent: Nov. 21, 2017

(54) REMOVABLE DEPLOYMENT SYSTEM AND METHOD FOR IMPLANTABLE MESH PROSTHESES

(71) Applicant: ATRIUM MEDICAL CORPORATION, Merrimack, NH (US)

(72) Inventors: David Filipiak, Nashua, NH (US); Albert A. Lepage, Jr., Nashua, NH (US)

(73) Assignee: Atrium Medical Corporation, Merrimack, NH (US)

( * ) Notice: Subject to any disclaimer, the term of this patent is extended or adjusted under 35 U.S.C. 154(b) by 132 days.

(21) Appl. No.: 14/644,611

(22) Filed: Mar. 11, 2015

(65) Prior Publication Data
US 2015/0257866 A1    Sep. 17, 2015

Related U.S. Application Data

(60) Provisional application No. 61/953,615, filed on Mar. 14, 2014.

(51) Int. Cl.
*A61F 2/00* (2006.01)
*A61L 27/28* (2006.01)
(Continued)

(52) U.S. Cl.
CPC .......... *A61F 2/0063* (2013.01); *A61L 31/048* (2013.01); *A61L 31/08* (2013.01);
(Continued)

(58) Field of Classification Search
CPC ............ A61F 2/0063; A61F 2002/0068; A61F 2002/0072; A61F 2210/0014; A61F 2210/0076; A61F 2230/0091; A61L 31/08
See application file for complete search history.

(56) References Cited

U.S. PATENT DOCUMENTS

| 5,304,187 A | 4/1994 | Green et al. |
| 8,124,127 B2 | 2/2012 | Faucher et al. |
| (Continued) | | |

FOREIGN PATENT DOCUMENTS

WO    2013/007535 A1    1/2013

OTHER PUBLICATIONS

Extended European Search Report in EP Application No. 13767588. 0, dated Oct. 12, 2015, 6 pages.
(Continued)

*Primary Examiner* — Todd J Scherbel
(74) *Attorney, Agent, or Firm* — Wesley Scott Ashton

(57) ABSTRACT

A medical device including a mesh prosthesis having a first mesh layer affixed to a second mesh layer along a perimeter area. An enclosure is defined between the first and second layers and extends inwardly from the perimeter area. An opening in the first layer passes through the first layer to the enclosure. A fixation guide template defines a guide pocket within the enclosure. A resilient deployment structure is removably disposed within the enclosure and extending toward the perimeter area. The resilient deployment structure has an elasticity that generates a resilient deployment force for urging the mesh prosthesis to a deployed configuration from a non-deployed configuration. A shield projection extends outwardly from a perimeter of the resilient deployment structure and is engaged within the guide pocket to prevent relative rotational movement between the resilient deployment structure and the mesh prosthesis. A method of using a medical device is also included.

20 Claims, 16 Drawing Sheets

(51) Int. Cl.
    *A61L 31/04*    (2006.01)
    *A61L 31/08*    (2006.01)
(52) U.S. Cl.
    CPC ............... *A61F 2002/0072* (2013.01); *A61F 2210/0004* (2013.01); *A61F 2210/0076* (2013.01); *A61F 2220/0016* (2013.01); *A61F 2230/0006* (2013.01); *A61F 2230/0091* (2013.01)

(56) References Cited

U.S. PATENT DOCUMENTS

| | | |
|---|---|---|
| 8,500,759 B2 | 8/2013 | Koyfman et al. |
| 2004/0019360 A1 | 1/2004 | Farnsworth et al. |
| 2006/0078586 A1 | 4/2006 | Ferraro et al. |
| 2009/0181937 A1 | 7/2009 | Faucher et al. |
| 2009/0192530 A1 | 7/2009 | Adzich et al. |
| 2009/0208552 A1 | 8/2009 | Faucher et al. |
| 2009/0326676 A1 | 12/2009 | Dupic et al. |
| 2011/0082479 A1* | 4/2011 | Friedlander ........... A61F 2/0063 606/151 |
| 2011/0224704 A1 | 9/2011 | Bailly et al. |
| 2013/0035704 A1 | 2/2013 | Dudai |
| 2014/0025093 A1* | 1/2014 | Horton ................. A61F 2/0063 606/151 |
| 2014/0088619 A1* | 3/2014 | Cardinale .......... A61B 17/0057 606/151 |

OTHER PUBLICATIONS

International Search Report and Written Opinion issued for International Application No. PCT/US2015/019889, dated Jun. 17, 2015, 18 pages.

* cited by examiner

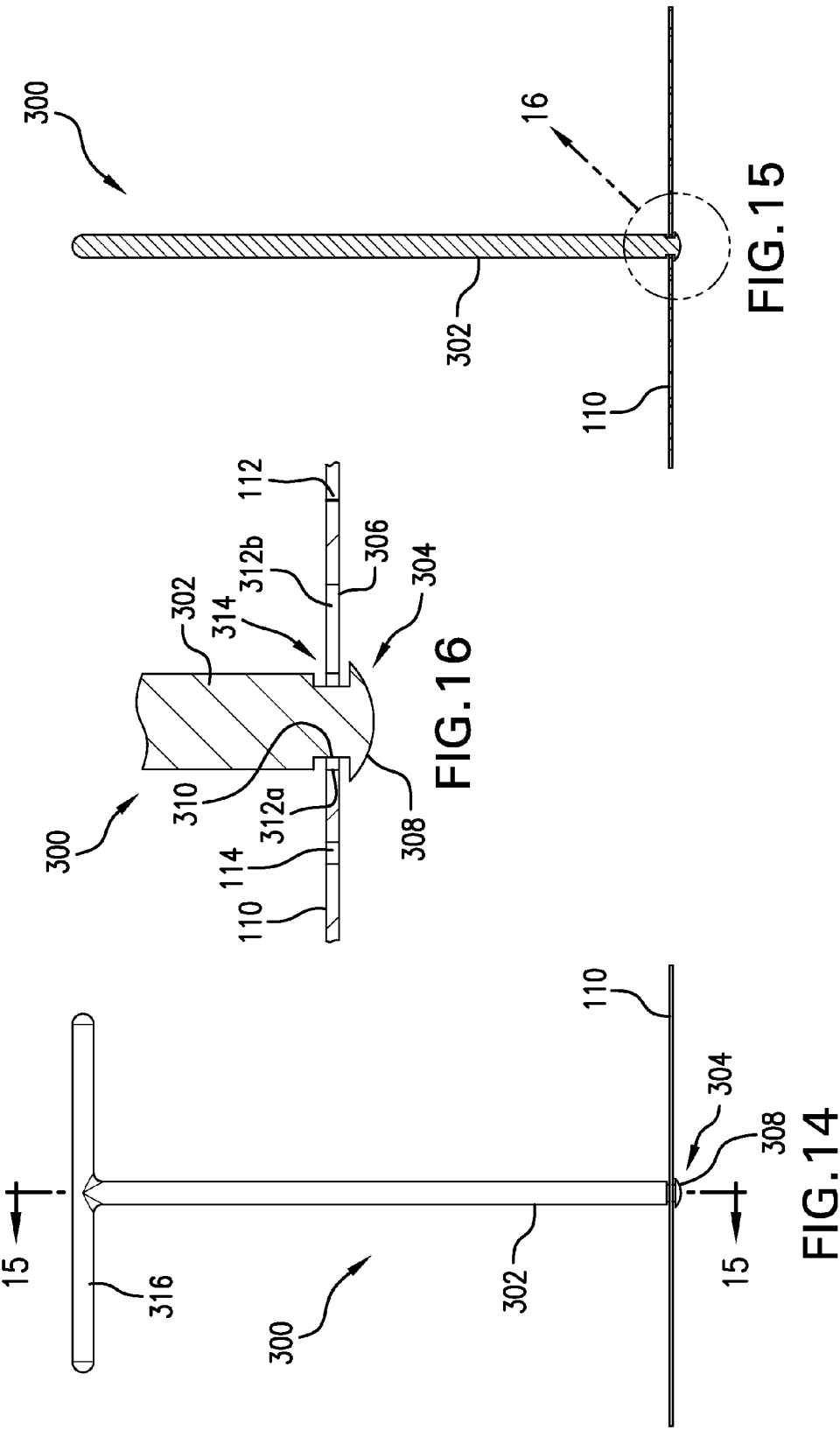

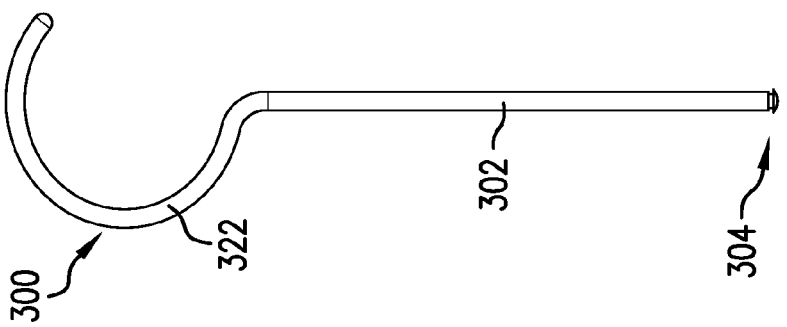
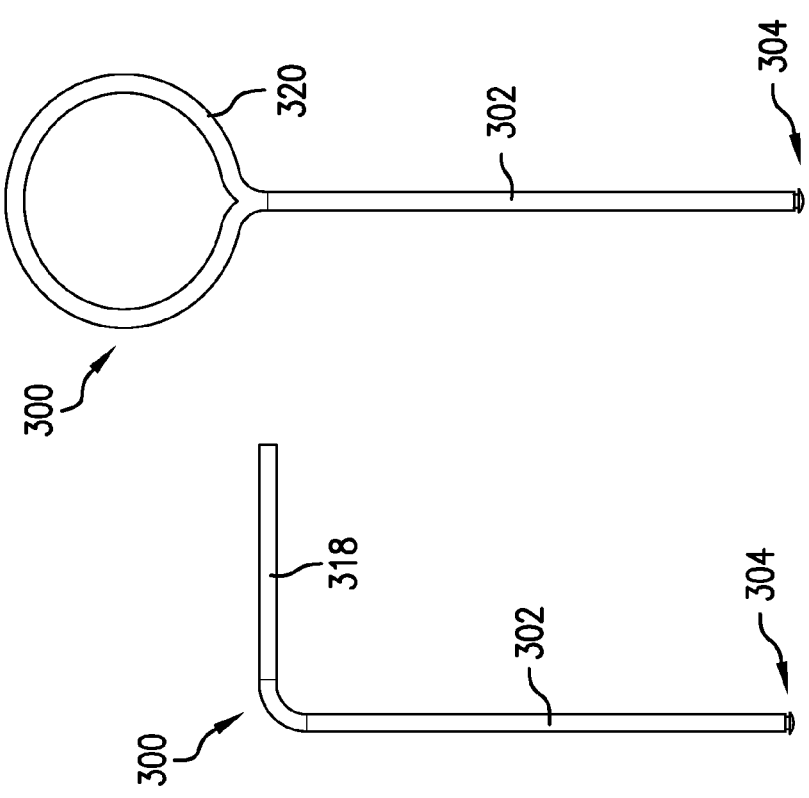
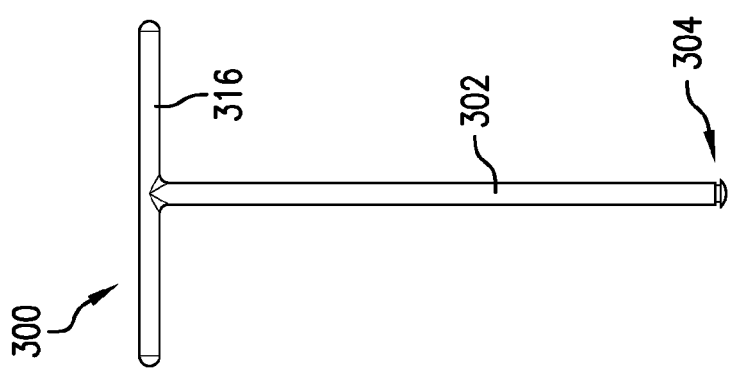

REMOVABLE DEPLOYMENT SYSTEM AND METHOD FOR IMPLANTABLE MESH PROSTHESES

CROSS-REFERENCE TO RELATED APPLICATIONS

This application claims the benefit of provisional application No. 61/953,615, filed Mar. 14, 2014 and is incorporated herein by reference.

FIELD OF THE INVENTION

The present invention relates to deployment devices, systems, and methods suitable for medical applications, such as open and laparoscopic ventral hernia repairs and small hernia repair (e.g., repair of umbilical or epigastric defects). More particularly, the present invention relates to a removable deployment structure configured to fit within an enclosure of a mesh prosthesis and serve as a surgical aid in the deployment, positioning, and fixation of the mesh prosthesis.

BACKGROUND OF THE INVENTION

Prostheses often are implanted during surgical or other medical procedures to aid in repair of defects, reinforcement of a target site, delivery of therapeutic, or to serve other medical purposes. For example, hernia patches or other similar prostheses are commonly implanted using open or laparoscopic techniques. Such techniques can be useful in treating central hernias as well as small hernias, e.g., umbilical or epigastral defects.

For instance, open procedures are performed by making a single incision through which a hernia patch is inserted for implantation to the target site. Typically, the hernia patch is rolled up or otherwise compacted prior to insertion so as to enable greater ease of passage through the single incision and to the site of the defect. Once the hernia patch is appropriately positioned within the body (e.g., in the abdominal cavity, in the pre-peritoneal space, etc.), it can be unfolded, unrolled, un-collapsed, or otherwise caused to assume a deployed, generally planar configuration.

However, deploying the hernia patch in this manner is a cumbersome task that requires skillful manual manipulation. Even then, it is often difficult for an adept surgeon given that such a task is performed under several layers of tissue. Furthermore, manipulation of the hernia patch can prove to be an even greater challenge in the case of laparoscopic procedures, since trocars used to implant the hernia patch provide limited range of motion, thereby requiring the surgeon to utilize small instruments and graspers.

Several existing mesh patches provide a base layer of mesh with second or third layers that form pockets, aprons, or other enclosures intended to aid in the manipulation and fixation of the mesh. Furthermore, among these, some mesh patches include a rigidified perimeter and/or a rigid ring or frame attached near a perimeter of the patch to cause the patch to assume a deployed, generally planar configuration once inserted into a patient. In some instances, the ring or frame is constructed from biodegradable material that can be absorbed over time. These absorbable rings or frames tend to lack sufficient strength or can potentially interfere with the intended functionality of the patch, e.g., tissue in-growth or reinforcement. In other instances, the ring or frame is formed of non-absorbable material (e.g., polypropylene, PTFE, etc.) and thus remains a permanent structure within the body. These patches tend to exhibit greater strength, but consequently may interfere with the functionality of the patch. For example, permanent rings can form additional contours that can create points of tension at particularly undesirable positions on the surface of the patch. Still other attempts to facilitate deployment provide a monofilament or wire ring that is crimped or sintered in order to adjoin the ends, which create yet additional weak points that historically have been associated with higher risk of failure, health complications, and even death after implantation.

Previous designs include a specifically engineered spiral tear channel for easy extraction of a resilient deployment structure from the mesh prosthesis. Also, some resilient deployment structure designs have a contiguous ring at the perimeter of the resilient deployment structure design that serves as visual confirmation of complete removal, and handle/deployment structure interplay to prevent premature tear extraction. However, current designs are limited in their control of lateral/rotational movement of the mesh prosthesis using the resilient deployment structure, as well as having limited ability to indicate preferred fixation sites.

SUMMARY

A medical device, including a mesh prosthesis having a first layer of mesh affixed to a second layer of mesh proximate to a perimeter area thereof; an enclosure defined between the first layer of mesh and the second layer of mesh and extending inwardly from the perimeter area of the mesh prosthesis; an opening in the first layer of mesh passing through the first layer of mesh to the enclosure; a fixation guide template defining a guide pocket within the enclosure; a resilient deployment structure removably disposed within the enclosure and extending toward the perimeter area, the resilient deployment structure having an elasticity that generates a resilient deployment force for urging the mesh prosthesis to a deployed configuration from a non-deployed configuration; and a shield projection extending outwardly from a perimeter of the resilient deployment structure and engaged within the guide pocket to prevent relative rotational movement between the resilient deployment structure and the mesh prosthesis.

In one embodiment, a method of using a medical device, the medical device having a resilient deployment structure disposed within an enclosure formed between a first layer of mesh and a second layer of mesh, includes locating the medical device in a deformed configuration at a first desired location; transitioning the medical device from the deformed configuration toward a deployed configuration due to a force exerted by the resilient deployment structure; transferring rotational forces from the resilient deployment structure to the mesh prosthesis due to engagement of a shield projection extending from the resilient deployment structure with a guide pocket formed within the enclosure by a fixation guide template to prevent independent rotation of the mesh prosthesis and the resilient deployment structure relative to each other; and positioning the mesh prosthesis to a second desired location by rotating the resilient deployment structure.

BRIEF DESCRIPTION OF THE FIGURES

These and other characteristics of the present invention will be more fully understood by reference to the following detailed description in conjunction with the attached drawings, in which:

FIG. 14 depicts a deployment device including the handle of FIG. 12 assembled with the support structure of FIG. 13;

FIG. 15 depicts a cross-section of the deployment device of FIG. 14 taken generally along section line 15-15;

FIG. 16 is an enlarged view of the area of FIG. 15 generally contained within the circle 16; and FIGS. 17-20 depict side views different shapes for the handle of the deployment device of FIGS. 14-16.

DETAILED DESCRIPTION

Figure 1A:
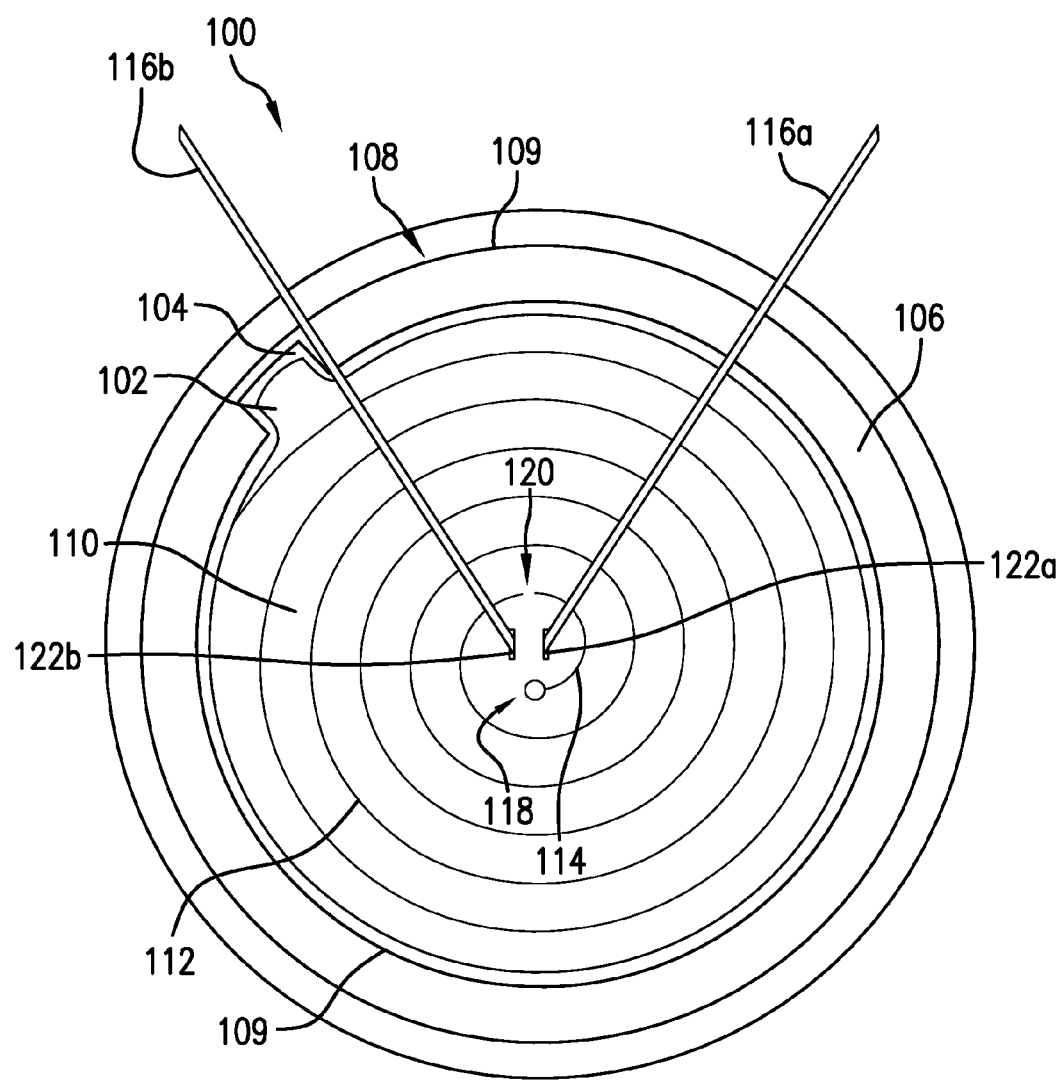
FIG. 1A depicts a schematic view of a deployment system with a resilient deployment structure having a shield projection that engages with a guide pocket of a mesh prosthesis, according to embodiments of the present invention.

An illustrative embodiment of the present invention relates to a resilient deployment structure capable of deploying a mesh prosthesis, such as a hernia patch, with a more elegant and efficient design than other conventional resilient deployment structures. The mesh prosthesis includes a first layer of mesh fixed to a second layer of mesh along a perimeter area in such a way that an enclosure extending from a central area of the mesh prosthesis to the perimeter area of the mesh prosthesis is formed. The first layer of mesh has an opening passing therethrough to the enclosure. The enclosure has a fixation guide template disposed along the perimeter area. The fixation guide template includes guide pockets extending laterally from the enclosure along the perimeter area and placed at predetermined fixation intervals. Alternatively, the fixation guide template may include one guide pocket. The resilient deployment structure is removably disposed within the enclosure and extends to the perimeter area. The resilient deployment structure has an elasticity that generates a deployment force. The deployment force causes the prosthesis to assume a deployed configuration from a non-deployed configuration. Also, shield projections are disposed along a perimeter of, and generally planar with, the resilient deployment structure. Alternatively, one shield projection may be disposed along the perimeter of the resilient deployment structure. Each of the shield projections are sized, dimensioned, and positioned to engage with the guide pockets of the fixation guide template in such a way that prevents rotational movement of the resilient deployment structure relative to the mesh prosthesis.

Accordingly, the deployment structure according to the illustrative embodiment of the present invention can have an elasticity that is sufficient for causing the mesh prosthesis to assume a deployed (e.g., generally planar and non-collapsed) configuration at a target site (e.g., fixation location/fixation site) even after being collapsed, compressed, or distorted in some manner (e.g., for implantation), and a flexibility sufficient for being removed from the mesh prosthesis.

As utilized herein, the term "flexible" adopts its conventional meaning in the art of the pliability of an object or extent to which an object permits bending. Flexible thus includes bending due to different types of deformation, e.g., elastic deformation, plastic deformation, or the like.

The term "elasticity" or "resiliency" generally refers to the ability of an object to reversibly deform under stress, as is well known in the art. Elasticity thus endows an object with the ability to return to its original shape after the removal of stress (e.g., one or more external forces) that produced deformation of the object, or otherwise inherently exert a force to urge the object back toward its default or original shape. Elasticity encompasses the ability of an object to return to a shape subsequent to deformation produced by expansion (e.g., elongation) and deformation produced by compression (e.g., as caused by folds, bends, etc. in an object).

FIGS. 1A through 9, wherein like parts are designated by like reference numerals throughout, illustrate example embodiments of a resilient deployment structure and a mesh prosthesis according to the present invention. In one embodiment, the resilient deployment structure includes some degree of flexibility such that it can be deformed into a deformed or non-deployed shape, e.g., rolled or folded, suitable for positioning within a cavity of a patient, and thereafter resiliently return to or resume a deployed shaped. Although the present invention will be described with reference to the example embodiments illustrated in the figures, it should be understood that many alternative forms can embody the present invention. One of skill in the art will appreciate many different ways to alter the parameters of the embodiments disclosed, such as the size, shape, or type of elements or materials, in a manner still in keeping with the spirit and scope of the present invention.

Figure 1B:
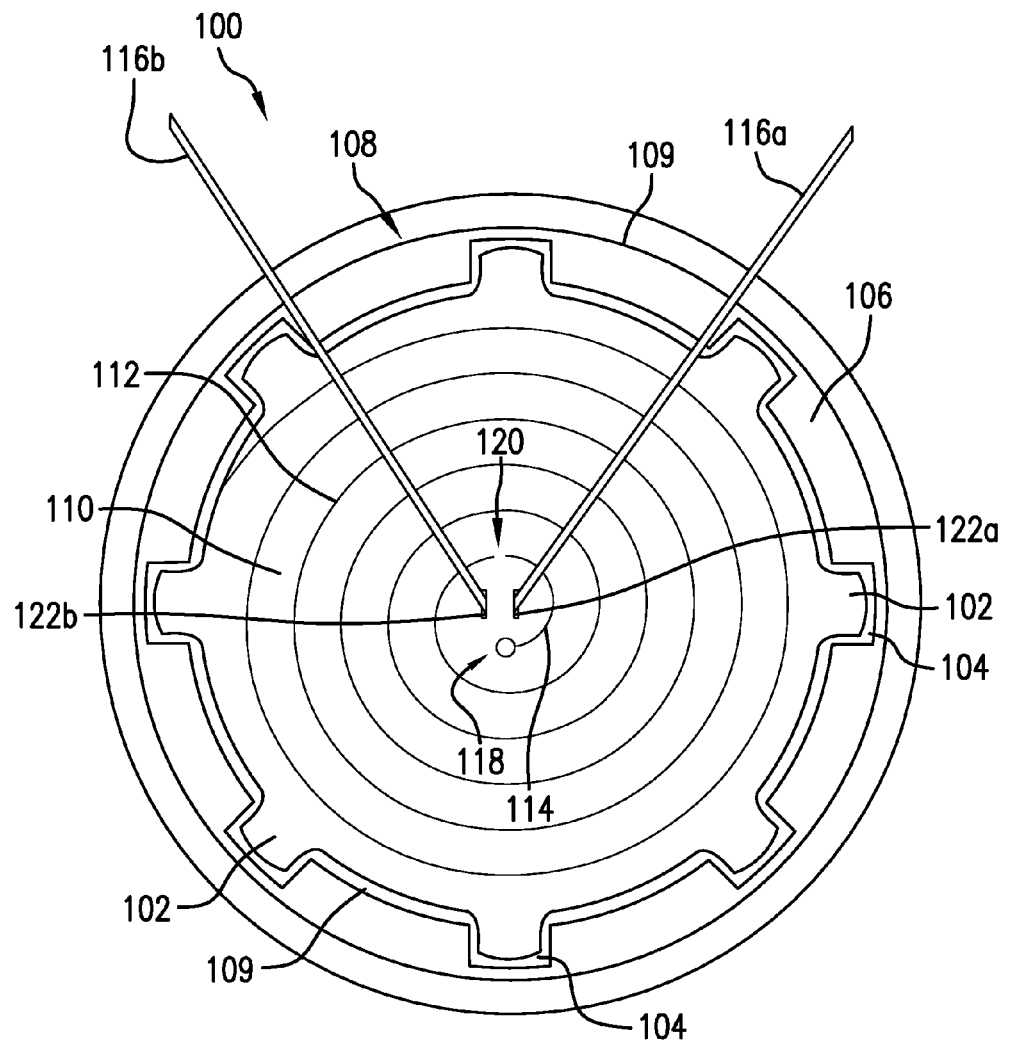
FIG. 1B depicts a schematic view of a deployment system with a resilient deployment structure having shield projections that engage with guide pockets of a mesh prosthesis, according to embodiments of the present invention.

FIGS. 1A-1B depict a perspective view of an example embodiment of a deployment system 100 according to the present invention. FIG. 1A depicts the deployment system 100 having one shield projection 102 and one guide pocket 104. FIG. 1B depicts the deployment system 100 having multiple shield projections 102 and multiple guide pockets 104.

Figure 3:
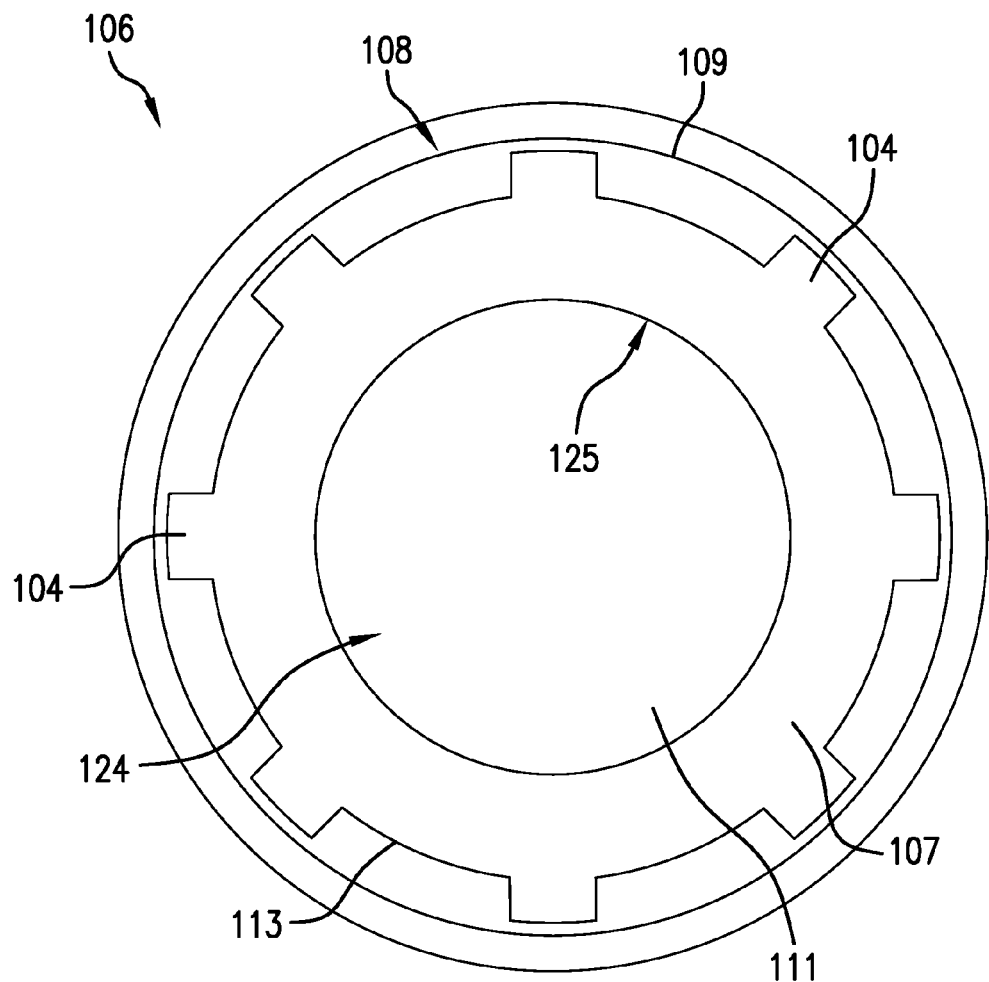
FIG. 3 depicts a schematic view of a mesh prosthesis having guide pockets, according to embodiments of the present invention.
Figure 4:
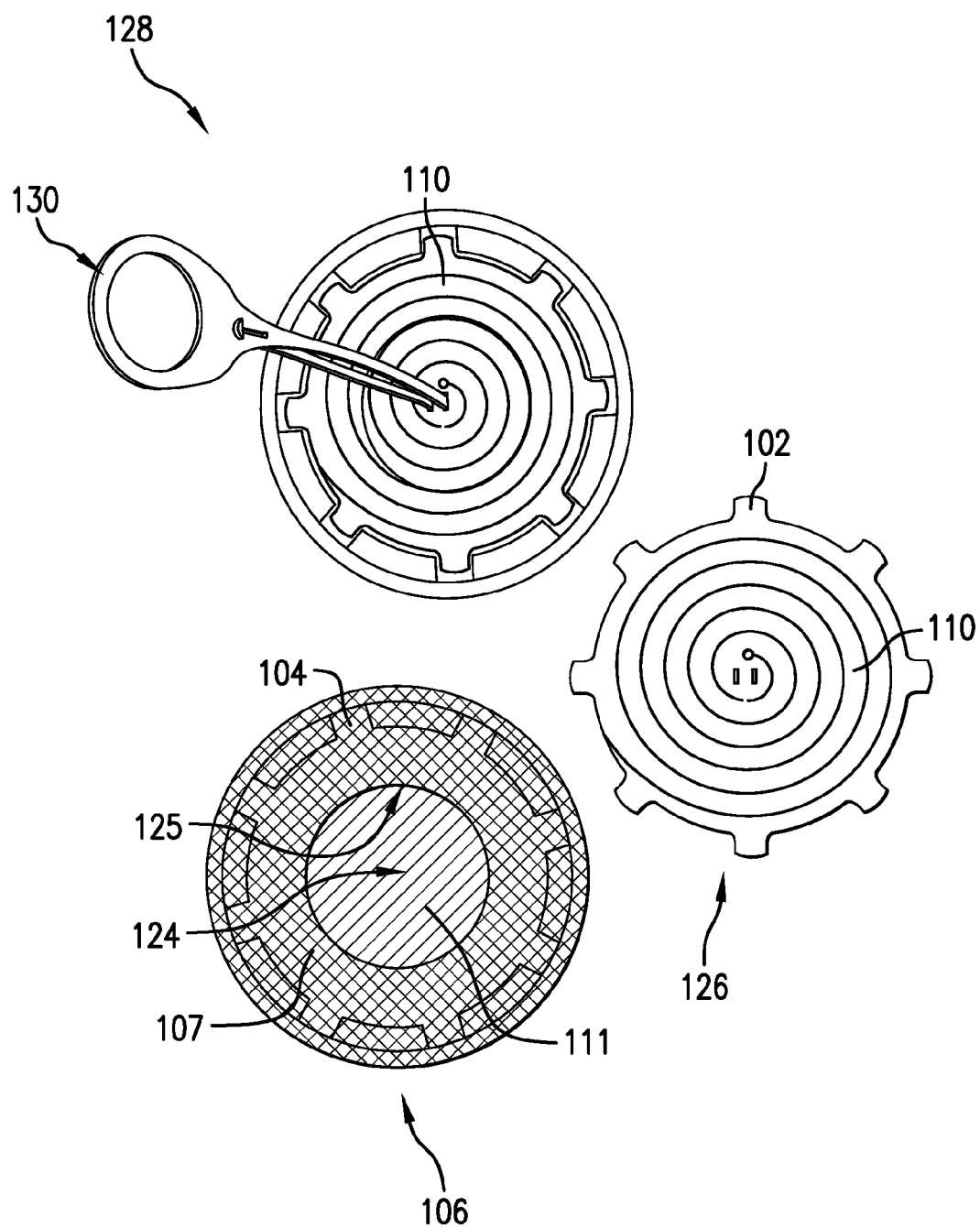
FIG. 4 depicts a photographic perspective view of an assembled deployment system alongside a disassembled deployment system, according to one aspect of the present invention.

The deployment system 100 includes a mesh prosthesis 106. As shown in FIGS. 3-4, the mesh prosthesis 106 has a first layer of mesh 107 fixed to a second layer of mesh 111 along a perimeter area 108 to form a central enclosure 125. For example, the first layer of mesh 107 can be fixed to the second layer of mesh 111 by being sewn or stitched to form stitching lines/sewn lines 109 along the perimeter area 108. By along the perimeter area 108, it is generally meant proximate to the perimeter area 108 and generally or at least partially following the shape of the perimeter area 108, albeit inwardly located from the outer perimeter. This stitching ensures substantial equivalence in edge material overhang and stitch strength holding the two mesh layers together along the perimeter. The first layer of mesh 107 has an opening 124 passing through to the enclosure 125. Disposed along the perimeter area 108 is a fixation guide template 113 (outline or stitching line of guide pockets 104). The fixation guide template 113 has guide pockets 104 extending laterally from the enclosure 125 along the perimeter area 108. The guide pockets 104 are placed at predetermined fixation intervals.

The deployment system 100 has a flexible, or resilient, deployment structure 110 that is removably disposed within the enclosure 125 of the mesh prosthesis 106. The resilient deployment structure 110 extends to the perimeter area 108 of the mesh prosthesis 106. The resilient deployment structure 110 has an elasticity that generates a deployment force. In particular, the deployment force causes the mesh prosthesis 106 to assume a deployed configuration (e.g., generally planar and non-collapsed) from a non-deployed configuration (e.g., folded up or rolled up upon itself). A deployed (e.g., generally planar) configuration of the resilient deployment structure 110 is characterized by an absence of folds, creases, bends, buckling, and the like in the resilient deployment structure 110. This deployed (e.g., generally planar) configuration of the resilient deployment structure 110 as described can cause the mesh prosthesis 106 to similarly assume a deployed (e.g., generally planar) configuration.

The deployment system 100 also has shield projections 102 disposed along a perimeter of, and generally planar with, the resilient deployment structure 110. Each of the shield projections 102 are sized, dimensioned, and positioned to engage with the guide pockets 104 of the fixation guide template 113 in such a way that prevents rotational movement of the resilient deployment structure 110 relative to the mesh prosthesis 106. For example, the shield projections 102 may be joined with the resilient deployment structure 110, e.g., formed integral therewith, affixed thereto, sewn thereto, stitched thereto, coupled thereto, fastened thereto, adhered thereto, or otherwise joined therewith.

The shield projections 102 may be positioned at equal interval distances from one another. Likewise, the predetermined fixation intervals between each of the guide pockets 104 may be at equal interval distances from one another. Alternatively, both the shield projections 102 and the predetermined fixation intervals between each of the guide pockets 104 may be a non-equal interval distances from one another, but should still match up with each other in a manner enabling the operation of each component as described herein.

The resilient deployment structure 110 can have a separation line 112 disposed in the resilient deployment structure 110 extending in a generally serpentine shape from a central portion of the resilient deployment structure 110 to a perimeter area along the perimeter of the resilient deployment structure 110. The separation line 112 may be composed of through-holes. Alternatively, the separation line 112 may include a continuous strip of material which cuts into the resilient deployment structure 110. Additionally, a through cut 114 may be disposed at an innermost end of the separation line 112 at a central portion of the resilient deployment structure 110.

A "serpentine separation line" herein refers to an arrangement of one or more connected separation lines that extend from an inner (e.g., central) portion of the resilient deployment structure 110 to one or more points on the perimeter of the resilient deployment structure 110. The term "serpentine" can include straight lines, jagged lines, curved lines, and the like. As utilized herein, a "separation line" generally refers to any straight, curved, jagged, etc. pathway situated in one or more materials that is adapted to be torn (e.g., without separating abutting portions in the one or more materials that are away from the separation line). A separation line can extend across one material or multiple different materials and can extend across one or multiple types of objects. In illustrative embodiments, the separation line 112 travels some angular distance relative to its inner endpoint (e.g., does not follow a straight line). The separation line may travel an angular distance of at least 360 degrees (e.g., by making at least one complete revolution). Furthermore, the separation line 112 is illustrated throughout the figures as a spiral separation line. The separation line can include and be implemented by a series of through-holes, a thin or weaker material, a partial cut or groove, or any other type of separation line. One of skill in the art will appreciate yet other materials, implementations, shapes, and the like for the separation line 112. All such alternatives are contemplated within the scope of the present invention. It should be noted that the separation line 112 can assume other types of serpentine shapes besides the exemplary smoothly curved serpentines and spirals depicted in the figures. For example, the separation line 112 can be shaped as square serpentines/spirals, other shaped serpentines/spirals, or combinations thereof.

The deployment system 100 can also include a handle assembly having first arm 116a and a second arm 116b. A pulling force applied to the first arm 116a initiates separation along the separation line 112 beginning at the through-cut 114. The first arm 116a may thus enable the functionality of a removal or release tool for the support structure 110. The second arm 116b is configured and positioned in such a way that a pulling force applied to the second arm does not initiate separation along the separation line 112 beginning at the through-cut 114. The second arm 116b may thus enable the functionality of a positioning tool for positioning the resilient deployment structure 110.

In one example, the separation line 112 may include an inner portion (e.g., proximate to the center) and an outer portion (e.g., proximate to the perimeter). If the separation line 112 is formed as a weakened section, groove, or cut, the separation line 112 at the inner portion can made to be relatively stronger (e.g., have a shallower cut or groove) than the separation line 112 at the outer portion, e.g., to promote more difficult initial separating/release along the inner portion (e.g., thus preventing unintentional separating/release until a user truly intends to remove the resilient deployment structure 110 and provide greater durability for the user to reposition or manipulate the structure 110), and easier separating/release along the outer portion (e.g., to facilitate the separation/release after separation has begun). The inner portion of the separation line 112 and the outer portion of the separation line 112 can be continuous with one another.

The separation line 112 can be preceded at its innermost end by the through-cut 114. The through-cut 114 can be a slit-like or slot-like opening situated in and extending entirely through the resilient deployment structure 110 (i.e., passing from a top surface of the resilient deployment structure 110 to a bottom surface of the resilient deployment structure 110). The through-cut 114 can follow a path that forms an extrapolation of the serpentine path followed by the separation line 112. Accordingly, the through-cut 114 effectively forms a flap that, when pulled upward, initiates release of the separation line 112. At an innermost end, the through-cut 114 may terminate at a stress relief hole 118. Functionally, the stress relief hole 118 is a hole situated at the beginning of the separation line 112 to effectively distribute the stress in this region and thereby reduce the likelihood of propagation of unintended separations in the resilient deployment structure 110 at non-perforated positions away from the separation line 112. At an outermost end, the through-cut 114 can terminate at a gap 120 of material on the resilient deployment structure 110 between the through-cut 114 and the innermost end of the separation line 112. For example, the gap 120 can have a thickness that is substantially equal to the thickness of the majority of the resilient deployment structure 110 (e.g., can have a thickness equal to the thickness of portions situated between the revolutions of the serpentine separation line 112).

Furthermore, the deployment system 100 is not limited to any particular density, thickness, etc. for the resilient deployment structure 110. For example, the resilient deployment structure 110 can be constructed of low density polyethylene, low density polypropylene, and the like. Furthermore, a wide variety of combinations of specific materials and structural properties (e.g., including number of revolutions of the separation line 112) can be selected to provide the resilient deployment structure 110 with a flexibility sufficient to reconfigure and pass through the opening 124 in the mesh prosthesis 106, such that the present invention is by no means limited to the specific embodiments illustrated.

In the example embodiment of FIGS. 1A-1B, the arm slots 122a, 122b can be distinguished based on proximity to the through-cut 114. Accordingly, the arms 116a, 116b similarly can be distinguished based on which arm slot 122a, 122b each passes through and extends from. By providing the through-cut 114 in a position displaced from the center of the resilient deployment structure 110, the arms 116a, 116b can be used for different functions by a surgeon during intraoperative handling and manipulation. The arm 116a, being more proximate to the through-cut 114 and less proximate to the thicker inner portion, will more effectively break the gap 120 of material and initiate release of the separation line 112 in response to a moderate tug or pull by the surgeon. Stated differently, tugging upward on the first arm 116a causes the semi-circular flap formed by the through-cut 114 to lift upward and eventually distribute enough tension on the gap 120 to separate the gap 120 and thereby initiate release of the separation line 112. On the other hand, the second arm 116b, being less proximate to the through-cut 114 (i.e, more distal from the through-cut 114) and more proximate to the thicker inner portion, will more effectively serve as a positioning tool which can better distribute tensile forces due to tugs and pulls without initiating release of the separation line 112.

A method of using deployment system 100 includes providing the mesh prosthesis 106 and providing the resilient deployment structure 110 with the shield projections 102. As described above, the resilient deployment structure 110 is disposed within the enclosure 125 of the mesh prosthesis 106 in such a way that the shield projections 102 engage with the guide pockets 104 of the mesh prosthesis 106. In this example, the mesh prosthesis 106 and resilient deployment structure 110 are initially constrained in a rolled, non-deployed, configuration by a constraining force. The deployment system 100 (mesh prosthesis 106 with the resilient deployment structure 110) is positioned at a desired location against an underlying tissue location. At this point, the constraining force of the mesh prosthesis 106 and the resilient deployment structure 110 is removed. The resilient deployment structure 110 applies a deployment force to the mesh prosthesis 106 to cause the resilient deployment structure 110 and the mesh prosthesis 106 to achieve an unrolled, deployed, configuration. In particular, the elasticity of the resilient deployment structure 110 causes the resilient deployment structure 110 and the mesh prosthesis 106 to "spring" back into (or otherwise assume) the deployed (e.g., generally planar) configuration.

The mesh prosthesis 106 is enabled to be rotationally positioned by rotating the resilient deployment structure 110 a desired amount. The mesh prosthesis 106 rotates the same desired amount or in tandem with the resilient deployment structure 110 by action of the shield projections 102 engaged with the guide pockets 104 which prevents the resilient deployment structure 110 from rotating independent of the mesh prosthesis 106. This improves handling characteristics and lateral or rotational placement of the mesh prosthesis during a surgery. More particularly, this prevents resilient deployment structure from slipping when rotated during positioning of the mesh prosthesis. In another example, the mesh prosthesis 106 can be positioned by forcing the resilient deployment structure 110 a desired distance at a radial or axial direction. This causes the mesh prosthesis 106 to advance the desired distance in the radial or axial direction.

Figure 2:
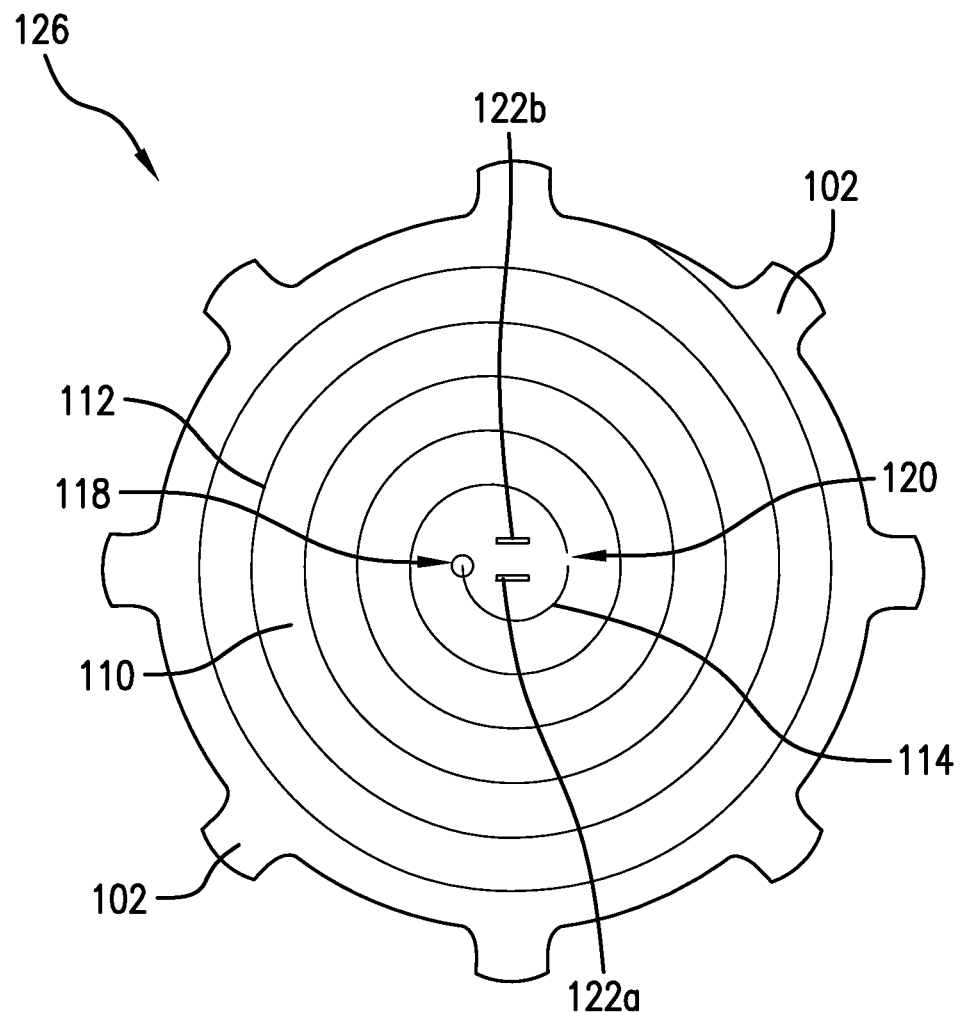
FIG. 2 depicts a schematic view of a mesh deployment device having shield projections, according to embodiments of the present invention.

FIGS. 2-4 depict a mesh deployment device 126 in a deployed configuration (e.g., a substantially flat, not folded up or rolled up upon itself). The mesh deployment device 126 includes a resilient deployment structure 110 and shield projections 102. In particular, the mesh deployment device 126 has a resilient deployment structure 110 configured for removable disposal within an enclosure 125 of a mesh prosthesis 106. The resilient deployment structure 110 has an elasticity that generates a deployment force for deployment of the mesh prosthesis 106. The shield projections 102 are disposed along a perimeter of, and generally planar with, the resilient deployment structure 110. Each of the shield projections 102 are sized, dimensioned, and positioned to engage with the mesh prosthesis 106 in such a way that prevents rotational movement of the resilient deployment structure 110 relative to the mesh prosthesis 106. The resilient deployment structure 110 and shield projections 102 can be constructed of extruded polypropylene, low density polyethylene (LDPE), other plastic material, monofilament material, sheet material, or any other suitable biodegradable or non-biodegradable material, as would be appreciated by one of skill in the art upon reading the present specification.

FIGS. 3-4 depict a mesh prosthesis 106 in a deployed configuration. The mesh prosthesis has a first layer of mesh 107 affixed to a second layer of mesh 111 along a perimeter area 108 in such a way that an enclosure 125 extends from a central area of the mesh prosthesis 106 to the perimeter area 108. In particular, the first layer and the second layer can be adjoined (e.g., affixed, coupled, adhered, fastened, sewn, stitched, or otherwise joined together) at a seam 109 (e.g., stitching line, welds, adhesive, or combinations thereof) of an outer perimeter area 108 of the mesh prosthesis 106. The mesh prosthesis 106 has an opening 124 formed in the first layer of mesh 107 and passing therethrough to the enclosure 125. Also, the mesh prosthesis 106 has a fixation guide template 113 forming at least a portion of the enclosure 125 and disposed along the perimeter area 108. The fixation guide template 113 has guide pockets 104 extending laterally from the enclosure 125 along the perimeter area 108 and placed at predetermined fixation intervals. The predetermined fixation intervals are distances between each of the guide pockets 104 along the fixation guide template. In particular, the predetermined fixation intervals may be equal interval distances or non-equal interval distances between each of the guide pockets 104. These fixation intervals can be predetermined based on the type of surgical procedure. For example, depending on the surgical procedure, a specific distance (i.e., predetermined fixation interval) between guide pockets 104 is determined such that the mesh prosthesis 106 can be successfully deployed and affixed over underlying tissue. This specific distance or predetermined fixation interval dictates the distance between each fixation site/fixation location 134 as described further below and illustrated in FIG. 7. The specific distance or interval is appreciated by those of skill in the art, and therefore particular quantities are not required or further discussed herein. The mesh prosthesis 106 can be constructed from polytetrafluoroethylene (PTFE), other suitable fluoropolymer materials, or any other suitable material.

Figure 5:
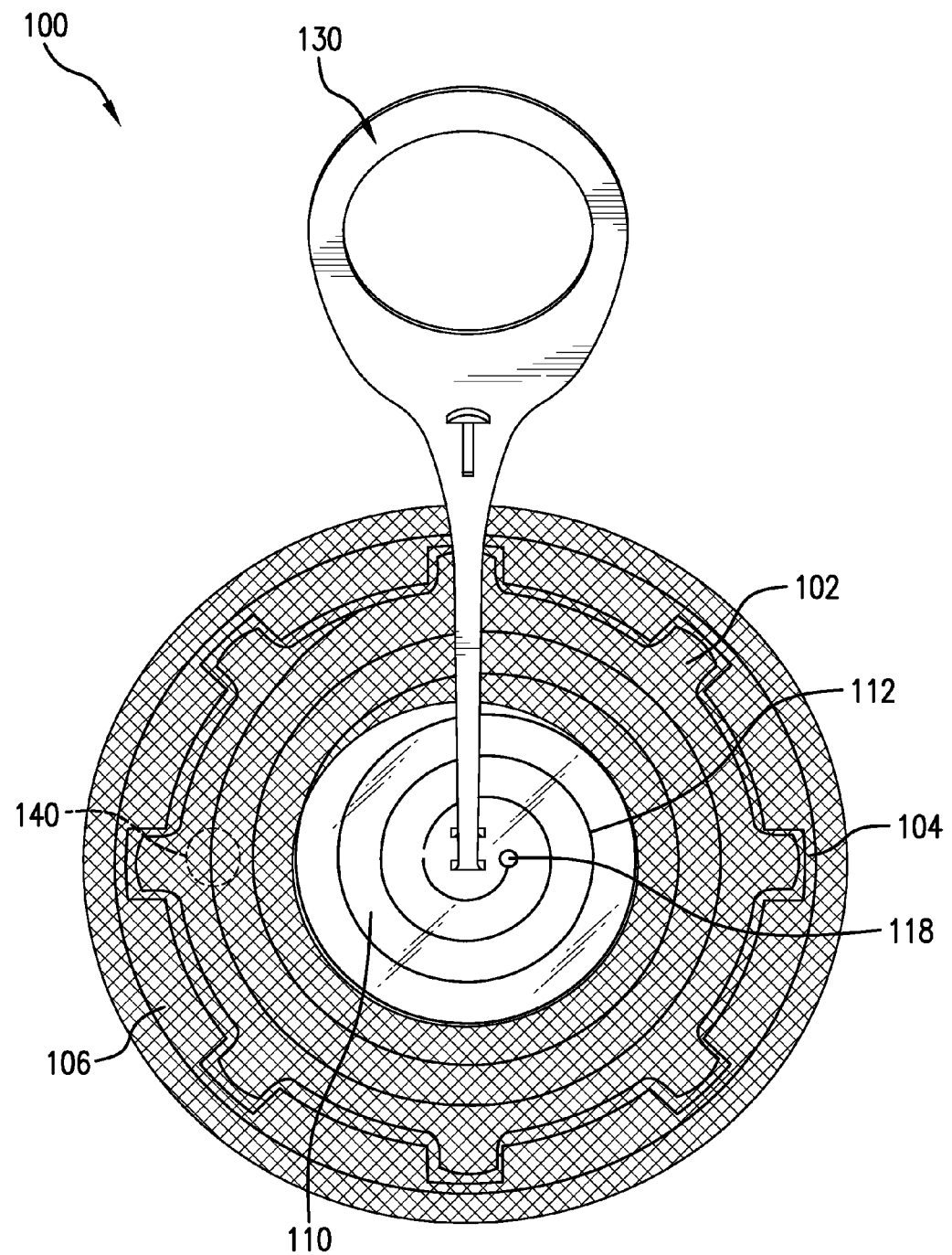
FIG. 5 depicts a photographic perspective view of the deployment system of FIG. 1B, according to one aspect of the present invention.

FIGS. 4-5 depict a disassembled (FIG. 4) and assembled (FIG. 5) deployment system 100 in accordance with the present invention. In particular, FIG. 4 depicts an example deployment kit 128. The deployment kit 128 includes a mesh prosthesis 106, a resilient deployment structure 110, and shield projections 102. In this example, the parts of the deployment kit 128 are assembled together to form the deployment system 100 in FIG. 5. As shown in FIGS. 4-7, an additional tool 130 may be coupled to the resilient deployment structure 110. The tool 130 can be configured as a positioning tool and a deployment device removal tool.

For example, kits according to other embodiments of the present invention each include one or more mesh deployment devices 126 each configured to be inserted into a mesh prosthesis 106, e.g., in a rolled or other collapsed configuration, or alternatively in a non-collapsed configuration. One of skill in the art will appreciate that there is no limit on the number of mesh deployment devices 126 and mesh prostheses 106 that are included in the kit. Furthermore, as alternatives, one or both of the mesh prosthesis 106 and the mesh deployment device 126 can be packaged and/or sold separately.

A resilient deployment structure 110, as depicted in FIG. 5, can be removed by providing a sharp pull on the tool 130 to begin separating a separation line 112 (e.g., through-holes or a continuous strip of material) at the stress relief hole 118, then by steadily pulling on the tool 130 in an upward direction away from the mesh prosthesis 106 to progressively separate the remainder of the separation line 112 extending out from the stress relief hole 118. In this manner, abutting portions along the separation line 112 of the resilient deployment structure 110 become disconnected and are enabled to release upward so as to assume a reconfigured (e.g., bent, folded, buckled, unraveled, overlapping, etc.) shape, e.g., resembling a helix or a conventional spiral staircase. The reconfigured shape allows the resilient deployment structure 110 to pass through the opening 124, which has a smaller total circumferential area than the total circumferential area of the resilient deployment structure 110 in the deployed (e.g., generally planar) state.

For example, the resilient deployment structure 110 may be configured in a helix configuration. Specifically, a user can remove the resilient deployment structure 110 through a hole or defect in an artificial muscle wall. In particular, after implanting the mesh prosthesis through the hole or defect and affixing it to the artificial muscle wall (e.g., with tacks or sutures). The ability of the resilient deployment structure 110 to reconfigure into a helix affords the mesh deployment device 126 great versatility. For example, this feature is particularly advantageous for the reason that it allows the mesh deployment device 126 to reconfigure in a manner enabling extraction through minimally sized defects or orifices. Also, the tool 130 may be used to rotate the mesh prosthesis 106 in tandem with the resilient deployment structure 110 to position the mesh prosthesis 106 as desired during implantation.

Figure 6:
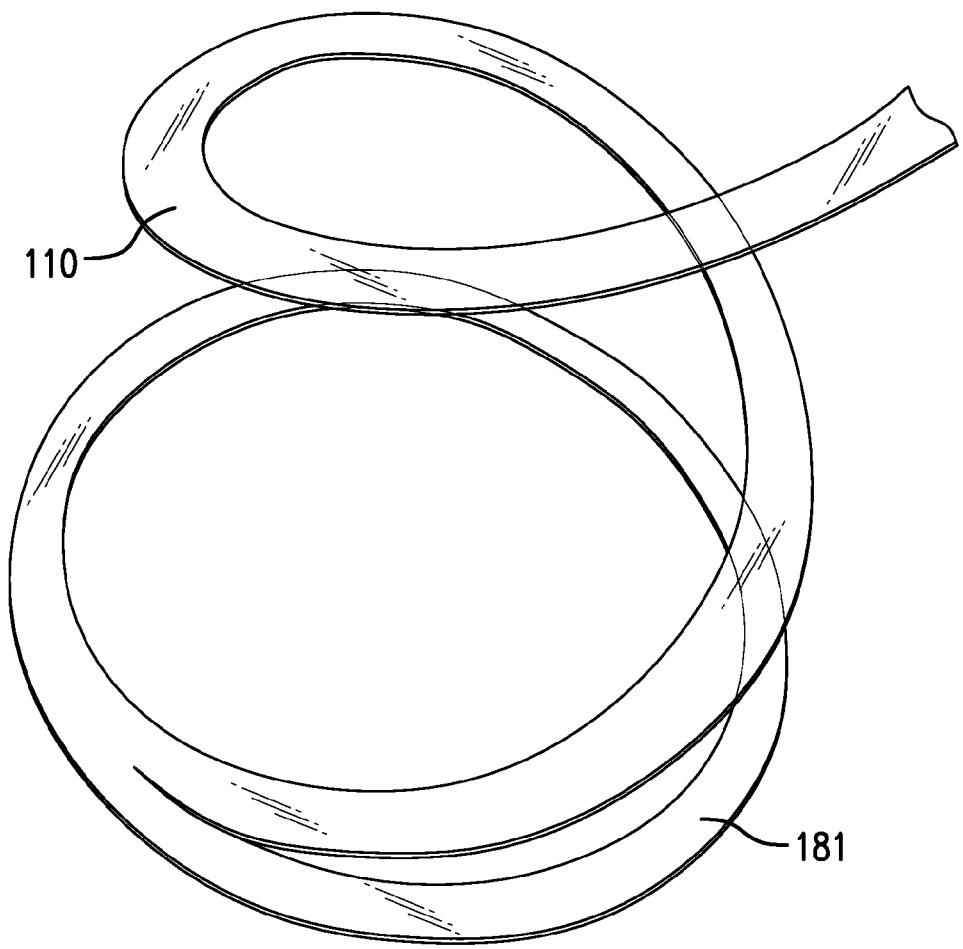
FIG. 6 depicts a close-up view of the resilient deployment structure with a ring configuration, according to one aspect of the present invention.

FIG. 6 depicts an example of the separation along the separation line 112 terminating at a ring configuration formed by the perimeter area 108 or perimeter of the resilient deployment structure 110. For example, a desired position 140, as shown in FIG. 5, on the resilient deployment structure 110 may be used as the location where the separation line 112 terminates to create the contiguous ring configuration. Specifically, the resilient deployment structure 110 is shown in FIG. 6 after having been reconfigured by separating the resilient deployment structure 110 along the separation line 12. The resilient deployment structure 110 terminates with a loop or ring 181. As shown and configured, the ring 181 is formed by the outer most perimeter of the resilient deployment structure 110. As the resilient deployment structure 110 is removed from the mesh prosthesis 106, the ring 181 is maintained at the end of an elongate continuous strip to signal to the user that the entire resilient deployment structure 110 has been removed from the prosthesis (once the user sees the ring 181 exiting from the mesh prosthesis 106 it is readily understood by the user that the entire prosthesis has been removed). Those of skill in the art will appreciate other ways to provide a signal or indication to the user of the last remaining portion of the resilient deployment structure 110 that is removed from the mesh prosthesis 106, including the ring 181 or some other structural variation, or a color or label indicator, or other visual representation indicating the end of the device or complete extraction of resilient deployment structure. An alternative example may include the separation along the separation line 112 terminating at a taper configuration, such as a thinning taper, formed by the perimeter area 108 or perimeter of the resilient deployment structure 110.

Figure 7:
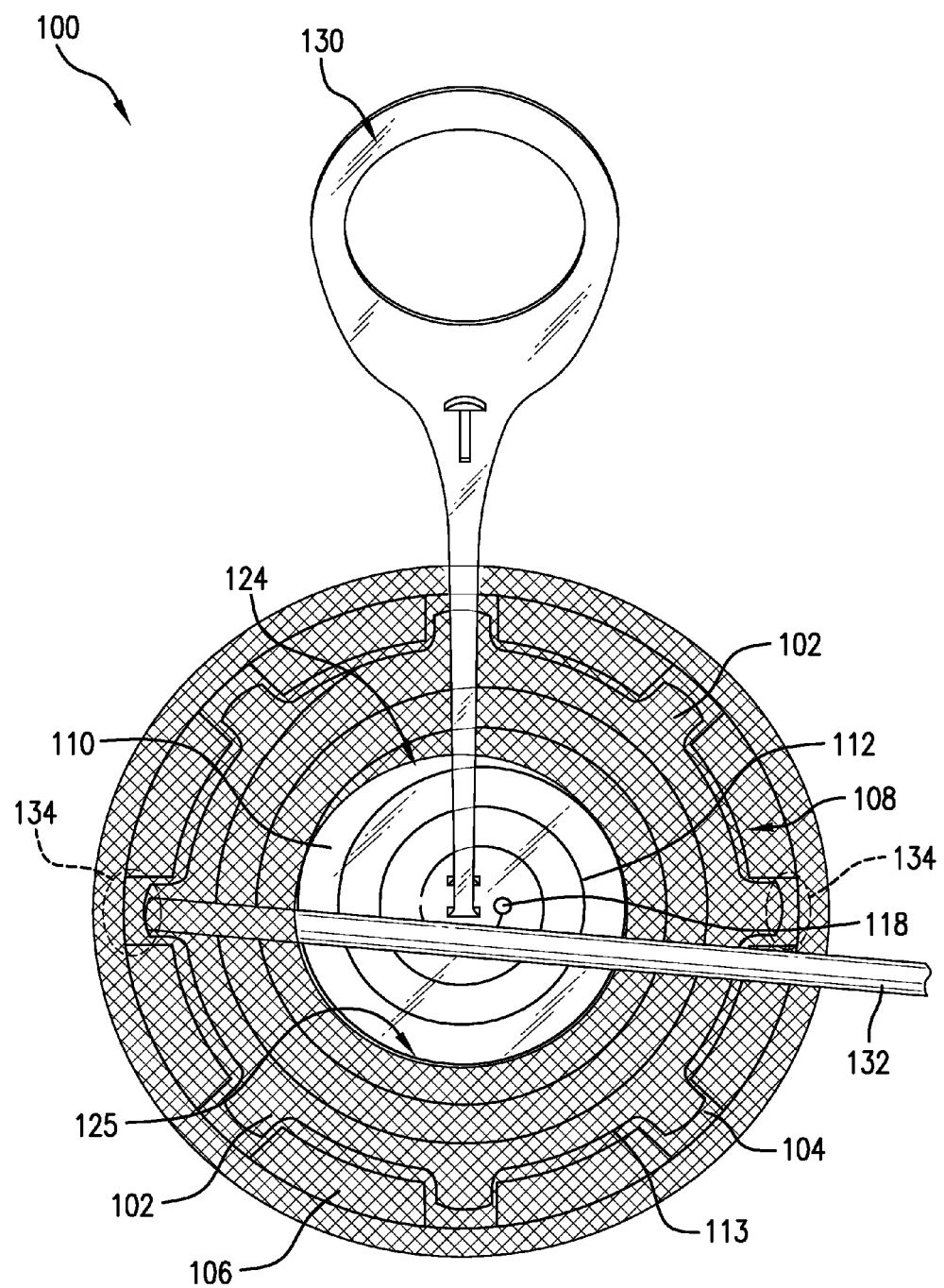
FIG. 7 depicts a perspective view of the deployment system being used to guide a fixation tool (e.g., tacker gun) to a fixation site, according to one aspect of the present invention.

FIG. 7 illustrates a fixation tool 132 being guided by the fixation guide template 113 of the resilient deployment system 100. As the fixation tool 132 is slid or dragged along the perimeter area 108, the tool moves in and out of the guide pockets 104. As noted herein, the guide pockets 104 are placed at predetermined fixation intervals, such that when the fixation tool 132 is positioned within a guide pocket 104, the user is alerted through tactile feedback of the fixation tool 132 moving into the guide pocket 104 that the fixation tool 132 is in a location suitable for fixation (i.e., a fixation site/fixation location 134). In particular, the deployment system 100 may be placed against underlying tissue for fixation thereto as part of a fixation process. The shield projections 102 provide a protective barrier between the fixation tool 132 that may be utilized during the fixation process and the underlying tissue when the fixation tool 132 is slid through the opening 124, into the enclosure 125, and along the fixation guide template 113 of the mesh prosthesis 106. The fixation tool 132 can be, for example, a tacker gun or suture needle, or other relatively sharp object, yet the present invention enables a user (e.g., surgeon) to blindly identify fixation sites/fixation locations 134 via tactile feedback as the fixation tool 132 moves along the fixation guide template 113.

In one example method of using the deployment system 100 with the fixation tool 132, as shown in FIG. 7, the fixation tool 132 is inserted in through the opening 124 into the enclosure 125 of the mesh prosthesis 106. A user, such as a surgeon, can slide the fixation tool 132 along the resilient deployment structure 110. The user can identify fixation sites/fixation locations 134 by tactile feedback through the fixation tool 132 as the fixation tool 132 is slid along the resilient deployment structure 110 into a guide pocket 104 extending laterally from the enclosure 125 along the perimeter area 108. During the identification of fixation sites/fixation locations 134, the shield projections 102 provide a barrier along which the fixation tool 132 slides. This barrier protects the underlying tissue location from abrasion by the sliding fixation tool. In particular, the barrier minimizes and prevents contact between fixation tools and underlying tissue (e.g., viscera, bowel) against which the mesh prosthesis 106 is placed. Also, the use of the fixation tool 132 can ensure accurate fixation symmetry which may prevent unbalanced tension or buckling at different regions along the perimeter area 108 of the mesh prosthesis 106.

Once the mesh prosthesis 106 has been secured to a fixation site/fixation location 134, the resilient deployment structure 110 can then be removed. To remove the resilient deployment structure 110, a tensile force is exerted on the resilient deployment structure 110 in a direction away from the enclosure 125 of the mesh prosthesis 106 causing the resilient deployment structure 110 to reconfigure (e.g., using the tool 130 as described further below, or using another surgical tool). This allows for the resilient deployment structure 110 to pass through the opening 124 in the mesh prosthesis 106. The tensile force is continually exerted until the resilient deployment structure 110 is removed from the enclosure 125 through the opening 124 of the mesh prosthesis 106. The resilient deployment structure 110 may be removed through the opening 124 in the mesh prosthesis 106. Thus, the opening 124 can have a total circumferential area that is less than the total circumferential area occupied by the resilient deployment structure 110 when the resilient deployment structure 110 is in an unrolled, deployed, configuration.

In general, methods according to the present invention are not limited to any particular fixation procedure. Rather, one of skill in the art will appreciate a wide variety of ways to use the deployment system 100, depending on the particular type of surgical procedure.

Figure 8:
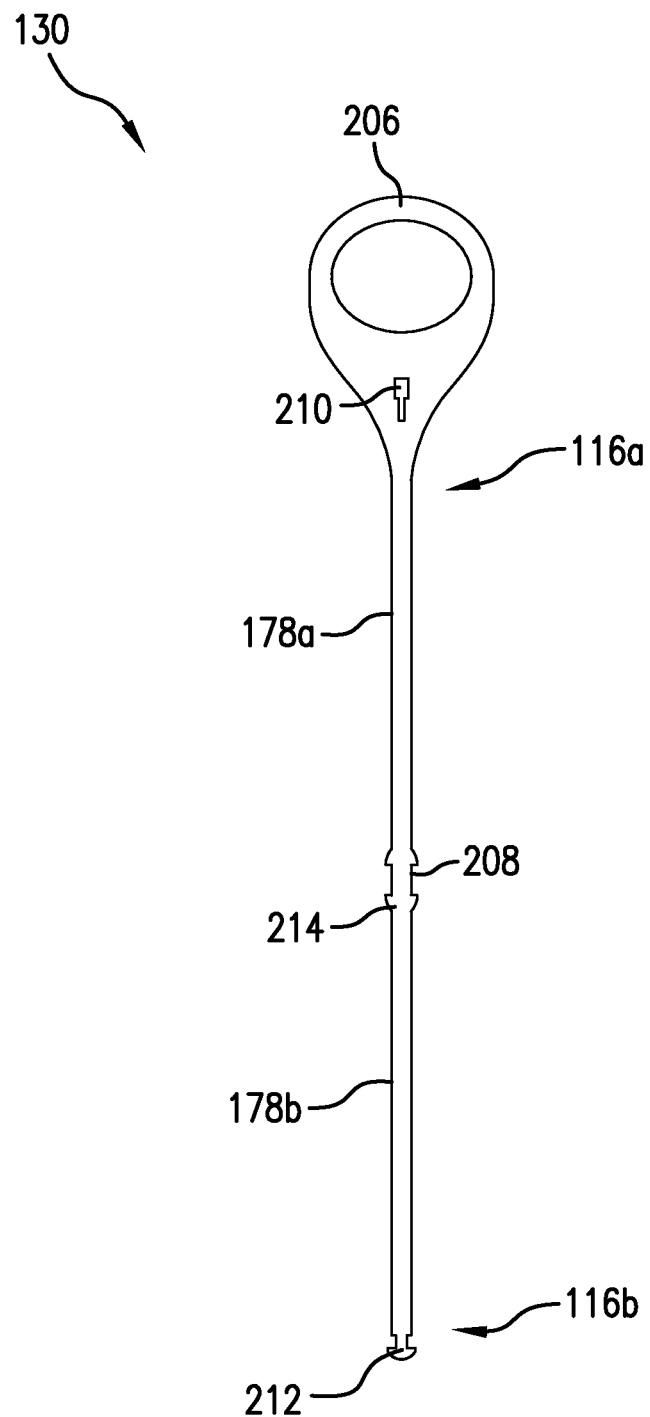
FIG. 8 depicts an arm in an unassembled (e.g., substantially flat) configuration that is adapted to serve as both a positioning tool and a deployment device removal tool, according to one aspect of the present invention.

FIG. 8 depicts the tool 130 configured as a positioning tool and a deployment device removal tool. The tool 130 may include a medial portion 208 that is slightly displaced from the center of the tool 130. The medial portion 208 thus divides the tool 130 into a longer appendage 178a and a shorter appendage 178b (relative to each other). As depicted in FIG. 8, the tool 130 is shown in an unassembled form, such that the appendages 178a, 178b are aligned along the same plane. To assemble the tool 130, the appendages 178a, 178b are bent at the outer edges of the medial portion 208, such that the appendages 178a, 178b are erect and upright. A finger support ring 206 is adapted to receive the finger of a user and is situated at the first arm 116a of the longer appendage 178a. Each appendage 178a, 178b includes one or more barb mechanisms 214 extending therefrom that, once slid through the arm slots 122a, 122b, act as mechanical stops that prevent the appendages 178a, 178b from sliding through the arm slots 122a, 122b in either direction. A slit 210 is situated in and through the first arm 116a of the longer appendage 178a, slightly inward of the finger support ring 206. The slit 210 is sized, shaped, and dimensioned to receive a protuberance 212 formed on the second arm 116b of the shorter appendage 178b. The protuberance 212 is sized, shaped, and dimensioned to pass through the slit 210 and subsequently lock in place by turning. The protuberance 212 is released by turning in the opposite direction to unlock. In illustrative embodiments, the tool 130 is formed of polypropylene, PETG (polyethylene terephthalate glycol-modified), or any other suitable (e.g., medical-grade) material. One of skill in the art will appreciate a variety of other materials herein that can be used to form the tool 130. All such alternatives and modifications are contemplated within the scope of the present invention.

Figure 9A:
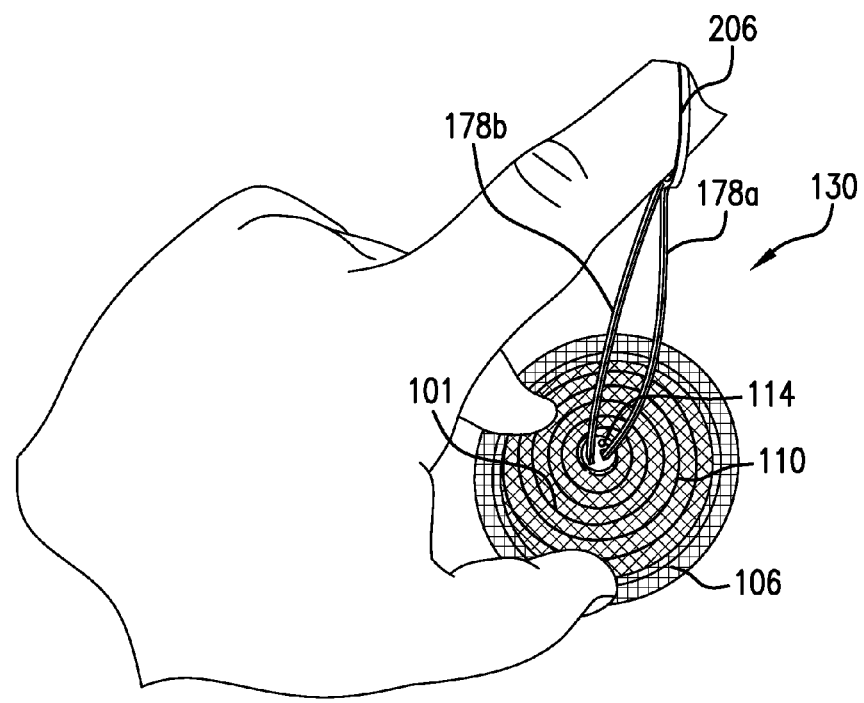
FIG. 9A depicts the arm of FIG. 8 in a resilient deployment structure situated in a mesh prosthesis, and in a locked position forming a positioning tool, according to aspects of the present invention.

FIG. 9A depicts the tool 130 of FIG. 8 coupled to the resilient deployment structure 110 of an example deployment device 101. The deployment device 101 is situated within a mesh prosthesis 106. The longer appendage 178a is adapted to be affixed to the resilient deployment structure 110 on the semi-circular flap formed by the serpentine through-cut 114, e.g., at the slot 122a. The shorter appendage 178b is adapted to be affixed at a location on the deployment device 101, but not on the semi-circular flap formed by the serpentine through-cut 114, e.g., at the slot 122b. The medial portion 208 of the arm 130 is situated such that the barb mechanisms 214 pass down through arm slots 122a, 122b to fixedly latch onto the resilient deployment structure 110.

As shown in FIG. 9A, the tool 130 is in a locked configuration. By locked configuration it is meant that the appendages 178a and 178b are secured or connected together. For example, the appendages 178a and 178b are connectable in one embodiment by inserting the protuberance 212 of the appendage 178b into the slit 210. When in the locked configuration of FIG. 9A, the tool 130 serves as a positioning tool, as described previously herein. Specifically, due to the differences in length, the shorter appendage 178b is taught, whereas the longer appendage 178a is bent and includes some slack. Thus, forces on the finger support ring 206 are distributed along the shorter appendage 178b when the tool 130 is in the locked configuration. Given that the appendage 178b is not affixed on the semi-circular flap formed by the serpentine through-cut 114, forces on the finger support ring 206 are distributed more evenly across resilient deployment structure 110 in a manner that tends to avoid initiating release of the serpentine separation line 112 when the arm 176 is in the locked configuration.

Figure 9B:
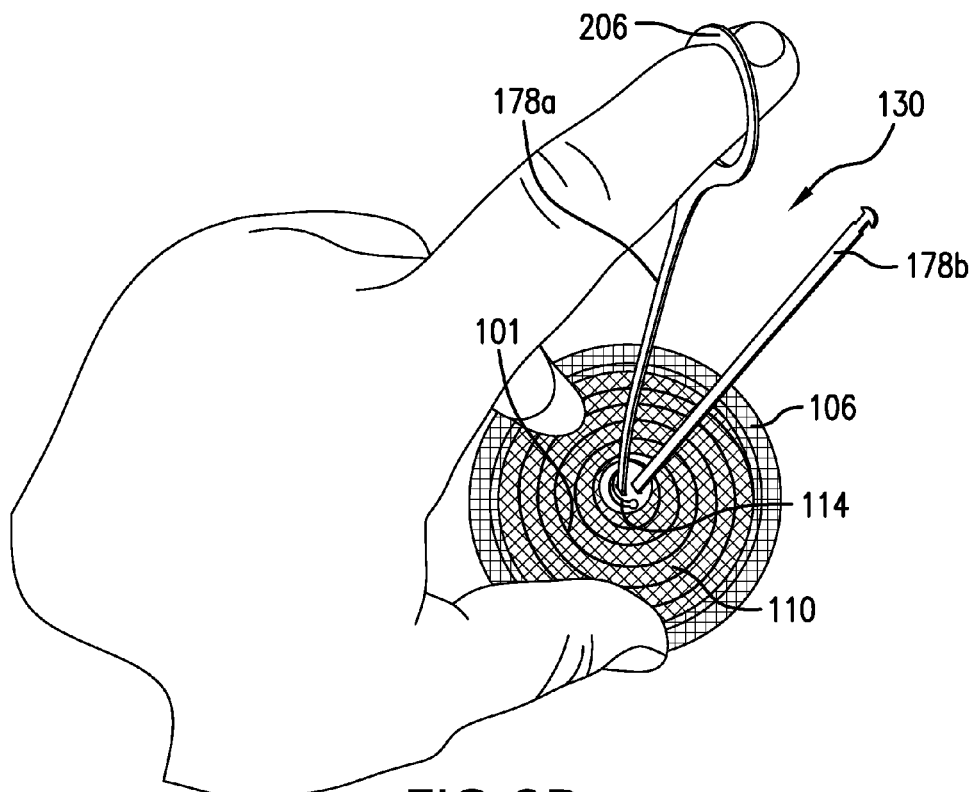
FIG. 9B depicts the arm of FIG. 8 in an unlocked position forming a deployment device removal tool, according to aspects of the present invention.

FIG. 9B depicts the tool 130 in an unlocked configuration. In the unlocked configuration, forces on the finger support ring 206 are distributed along the longer appendage 178a. Thus, the resulting tensile forces on the resilient deployment structure 110 are distributed on the semi-circular flap formed by the serpentine through-cut 114. This focusing of tensile forces on the semi-circular flap formed by the serpentine through-cut 114 enables the semi-circular flap to be lifted in such a way as to separation the gap 120 and initiate separation of the serpentine separation line 112. Accordingly, when the tool 130 is in a locked configuration, the tool 130 effectively serves as a positioning device, whereas when the tool 130 is in an unlocked configuration, the tool 130 effectively serves as a tab for removing the deployment device 101 from the mesh prosthesis 106.

Portions of the mesh prosthesis 106 and the resilient deployment structure 110 generally can take on a wide range of shapes, relative dimensions, and/or sizes. For example, FIGS. 10A through 10D depict additional embodiments of the mesh prosthesis 106 and the resilient deployment structure 110. One of skill in the art will appreciate that these examples are provided for purposes of further illustration and are not intended as limiting.

Figure 10A:
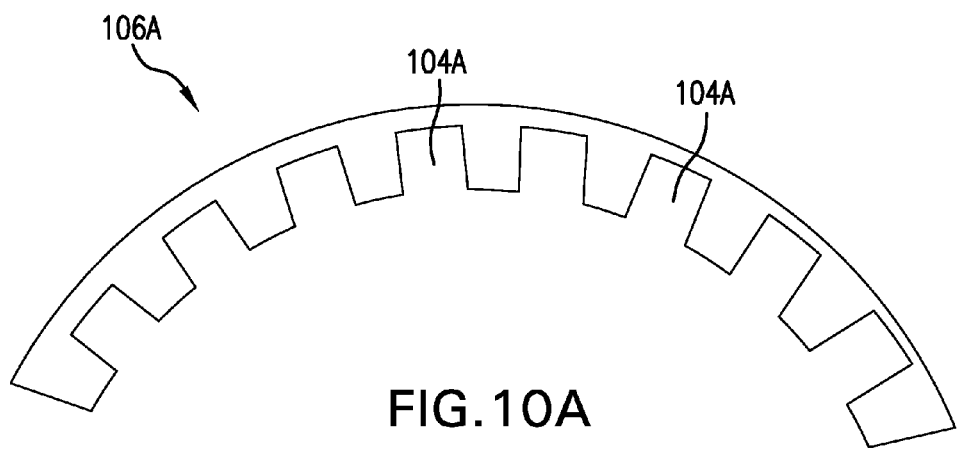
FIGS. 10A through 10D depict schematic views of the mesh prostheses with guide pockets having a variety of shapes, according to aspects of the present invention.
Figure 10B:
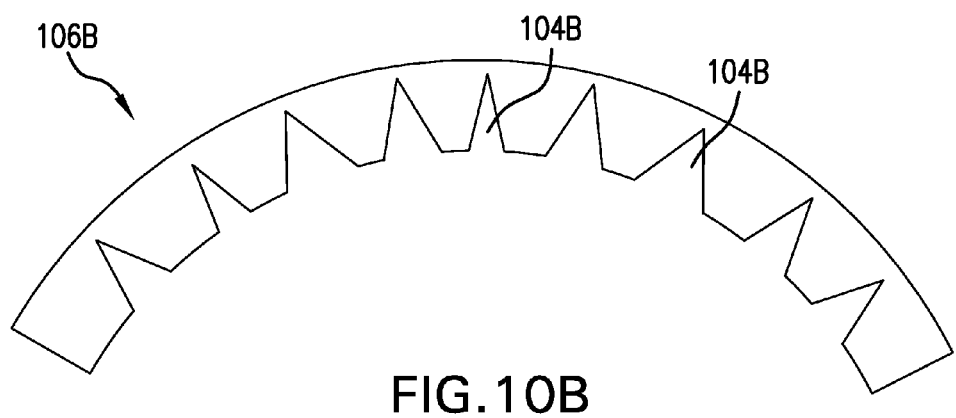
Figure 10C:
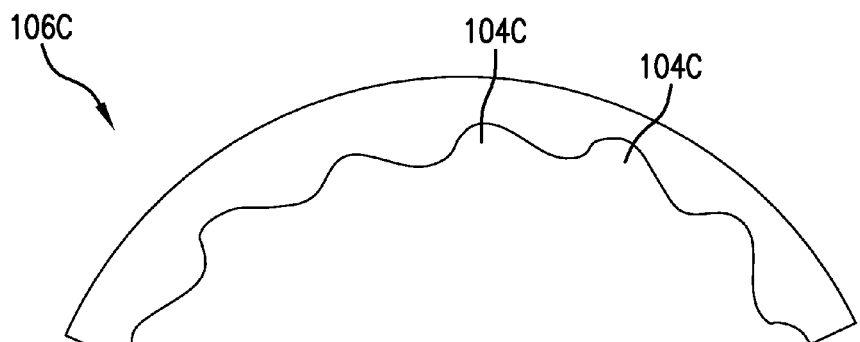
Figure 10D:
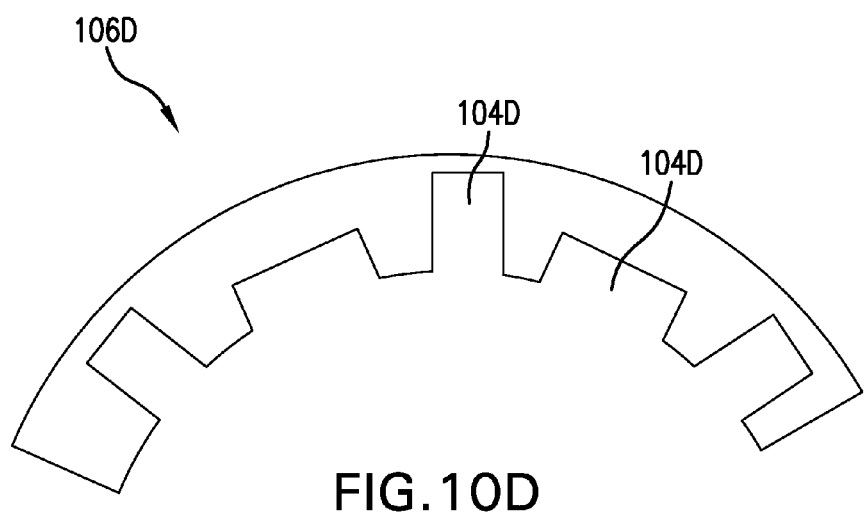

FIGS. 10A through 10D depict portions of the mesh prostheses 106 with guide pockets 104 having various shapes. FIG. 10A illustrates a portion of a mesh prosthesis 106A having guide pockets 104A that have a generally square shape. Correspondingly, the shield projections 102 can have a generally square shape with rounded corners to fit within the square guide pockets 104A. In another example, FIG. 10B illustrates a portion of a mesh prosthesis 106B having guide pockets 104B that have a generally triangular shape (e.g., V-shape). The generally triangular shaped guide pockets 104B can have the same or a variety of different angles and/or depths as known by one of skill in the art. Correspondingly, shield projections 102 for this triangular shaped example can have a generally triangular shape (e.g., V-shape) to fit within the triangular shaped guide pockets 104B. In another example, FIG. 10C illustrates a portion of a mesh prosthesis 106C having guide pockets 104C that have a generally scalloped shape. The generally scalloped shape guide pockets 104C can have the same or a variety of different radii and/or depths as known by one of skill in the art. Correspondingly, the shield projections 102 for this scalloped example can have a wavy shape rounded to fit within the scalloped shape guide pockets 104C. In another example, FIG. 10D illustrates a portion of a mesh prosthesis 106D having guide pockets 104D that have a generally rectangular shape. The generally rectangular shape guide pockets 104D can have the same or a variety of different lengths and/or widths as known by one of skill in the art. Correspondingly, the shield projections 102 for this example can have a generally rectangular shape and may have rounded corners to fit within the rectangular shape guide pockets 104D. One of skill in the art can appreciate other shape variations for guide pockets and corresponding shield projections, such that the mesh prosthesis interacts with the resilient deployment structure as intended by this description.

Figure 11:
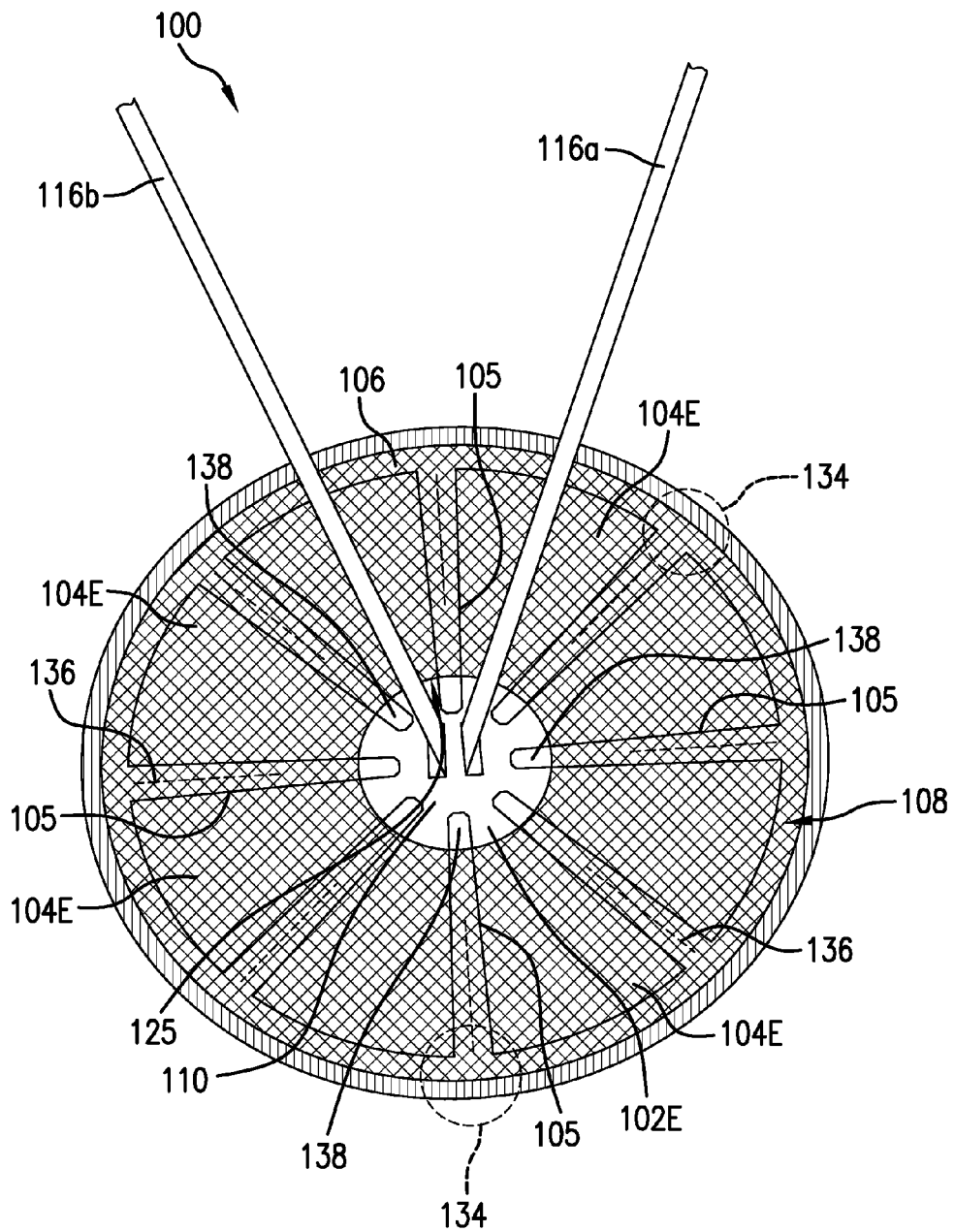
FIG. 11 depicts a perspective view of a deployment system having stitching for guiding a tool to fixation sites, according to embodiments of the present invention.

FIG. 11 illustrates another example of a deployment system 100. The deployment system 100 includes a resilient deployment structure 110 in a deployed (e.g., generally planar) configuration in a mesh prosthesis 106.

This deployment system 100 includes a mesh prosthesis 106 diagrammatically parsable into sections having substantially equal areas. The sections form guide pockets 104E. Also, the mesh prosthesis 106 has an enclosure 125 extending substantially to a perimeter area 108 of the mesh prosthesis 106. The system also has a resilient deployment structure 110 removably disposed within the enclosure 125 and extending to the perimeter area 108 of the mesh prosthesis 106. The resilient deployment structure 110 has gaps 138 that split the resilient deployment structure 110 into shield projections 102E being sized, dimensioned, and positioned to engage with the guide pockets 104E of the mesh prosthesis 106 in such a way that prevents rotational movement of the resilient deployment structure 110 relative to the mesh prosthesis 106. In particular, the resilient deployment structure 110 includes gaps 138 separating the resilient deployment structure 110 into sections that form shield projections 102E that are generally pie-shaped. The shield projections 102E are disposed within the guide pockets 104E that are generally pie-shaped.

The guide pockets 104E are defined or formed by radially oriented walls 105. In general, the radially oriented walls 105 are formed by joining the first layer of mesh 107 to the second layer of mesh 111. In one example, the radially oriented walls 105 are formed by stitches, welds, adhesive, or combinations thereof, which couple the first layer of mesh 107 to the second layer of mesh 111. Each wall is created with a stich 136 affixing a first layer of mesh 107 to a second layer of mesh 111. The stitch 136 is positioned to match up with the gaps 138 of the resilient deployment structure 110. The stitch 136 along each of the gaps 138 enables identification of fixation sites/fixation locations 134. In particular, the stitches 136 along the gaps 138 between the first layer of mesh 107 and the second layer of mesh 111 provide a guide for users (e.g., surgeons) to locate fixation sites/fixation locations 134 using the methodology described herein. The length of each stitch 136 can vary. Additionally, the stitches 136 allow a user to use tactile feedback to feel/catch the corner of the mesh prosthesis 106 for fixation or tacking. As would be appreciated by one of skill in the art, the structure of the embodiment shown in FIG. 11 creates relatively large pockets along the perimeter area 108 where fixation can be attempted versus the relatively smaller and more precisely positioned guide pockets 104 shown in the other figures and accompanying description. The guide pockets 104 shown in the present figure enable a user to have more freedom in selecting where exactly to affix the mesh prosthesis 106 to the underlying tissue.

Figure 12:
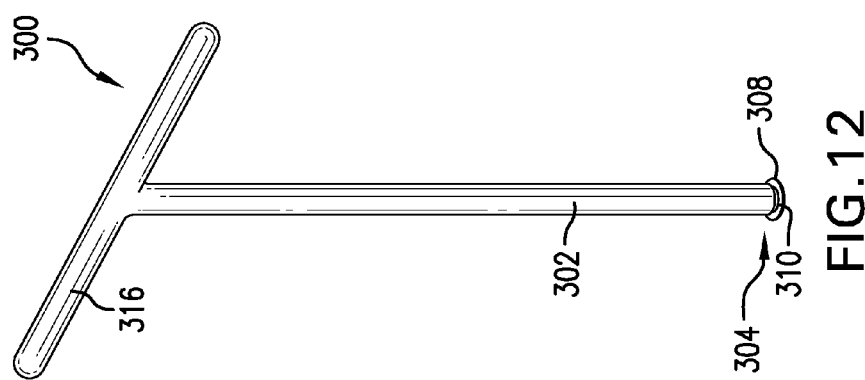
FIG. 12 depicts a handle of a deployment device according to an embodiment disclosed herein.

It is to be appreciated that the tool 130 having the arms 116a and 116b is a non-limiting example of a tool that can be included by and/or used with the deployment system 100, therefore, other tools may be used additionally or alternatively to those described above. For example, FIGS. 12 and 17 illustrate a tool 300 that can be used, e.g., in lieu of the tool 130, in order to enable a user to position, move, or otherwise manipulate the deployment system 100. The tool 300 includes an arm 302 terminating at one end in a connector 304.

Figure 13:
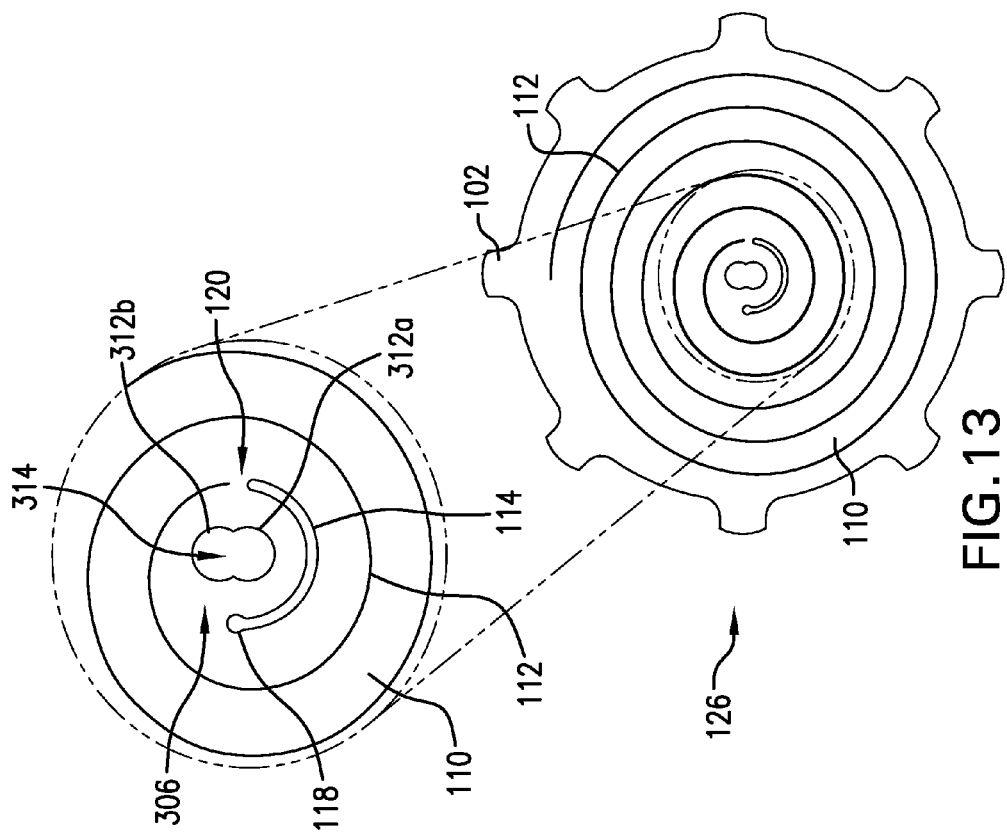
FIG. 13 depicts a support structure of a deployment device arranged for engagement with the handle of FIG. 12.

The connector 304 is arranged to enable the tool 300 to be connected to the support structure 110 of the deployment system 100. For example, FIG. 13 illustrates the support structure 110 of the deployment system 100 configured with an opening 306 that is arranged to receive the connector 304 of the tool 300. In one embodiment, such as the illustrated embodiment of FIGS. 12-16, the connector 304 may include a head 308, e.g., a flange, cap, shoulder, lip, etc., that is connected to the arm 302 via a recessed portion 310. The dimensions of the head 308 and the arm 302, e.g., the radial dimensions, may be selected such that they are greater than the corresponding size of the opening 306. In this way, for example, after the head 308 is snapped, pressed, squeezed, forced, or otherwise passed or positioned through the opening 306, the relatively larger dimensions of the head 308 and the arm 302 prevent, or otherwise frustrate or make more difficult, disengagement of the connector 304 from the opening 306. Those of skill in the art will recognize other permanent and releasable mechanical fasteners, adhesives, etc., that may be employed by the connector 304 in non-illustrated embodiments.

The shape of the opening 306 in one embodiment may be defined by two partially overlapping circular portions 312a and 312b (collectively, the "circular portions 312"). It is noted that the opening 306 may take other shapes, e.g., a single circle, an ellipse, a square, a triangle, etc. The partial overlap between the circular portions 312 creates a restriction or restricted area 314 of the opening 306 between the circular portions 312. In order to prevent the aforementioned disengagement of the connector 304 from the opening 306, the dimension or size of the circular portions 312 can be selected so that they are smaller than the corresponding dimensions, e.g., diameters, of the head 308 and the arm 302, but larger than or equal to the dimensions of the recessed portion 310. The restriction 314 may be sized in one embodiment such that it is the same size or smaller than the corresponding dimension, e.g., diameter, of the recessed portion 310 in order to prevent the tool 300 from freely moving between engagement with the portions of the opening 306 defined by the circular portions 312. Instead, the restriction 314 assists in holding the tool 300 in engagement with the portion of the opening 306 defined by a single one the circular portions 312. However, the restriction 314 may be sized such that if a suitable force is applied, the recessed portion 310 can be forced through the restriction 314 and into the portion of the opening 306 defined by the opposite one of the circular portions 312 (e.g., to transition the recessed portion 310 between engagement within the circular portion 312a to engagement within the circular portion 312b, and back).

For example, the circular portion 312a may be arranged similar to the slot 122a (that is, positioned relatively proximal to the through-cut 114), while the circular portion 312b is arranged similar to the slot 122b (that is, positioned relatively distal from the through-cut 114). In this way, the tool 300 can function similar to the tool 130 having the arms 116a and 116b discussed above. That is, for example, when the tool 300 is arranged in the portion of the opening 306 defined by the circular portion 312a, forces can be more readily applied to the semi-circular flap formed by the through-cut 114 in order to assist in severing or separating the material of the support structure 110 located at the gap 120, which starts the unraveling of the support structure 110 as described above, e.g., into a continuous strip along the path defined by the separation line 112. Likewise, similar to the slot 122b, the circular portion 312b is positioned relatively distal from the through-cut 114. In this way, forces applied to the support structure 110 when the tool 300 is engaged in the opening 306 at the circular portion 312b (similar to the arm 116b at the slot 116b) are more evenly distributed to the support structure 110 instead of being concentrated at the material at the gap 120, such that the tool 300 can be used to reposition the deployment system 100 without a great risk of severing the material at the gap 120. It is thus noted that moving the tool 300 between engagement with the circular portions 312a and 312b results generally in the same functionality as locking and unlocking the appendages 178a and 178b as discussed above.

As shown in FIGS. 12, 14, and 17, the tool 300 may include a cross-bar 316, giving the tool 300 a shape generally resembling a T. For example, the cross-bar 316 may assist a user in grabbing or gripping the tool 300 in order to apply a force thereto suitable for unraveling the support structure 110. It is to be appreciated, however, that other shapes for the tool 300 are also possible. For example, FIGS. 18-20 show various other shapes for the tool 300. For example, in FIG. 38 the tool 300 has an extension 318 extending transversely from the arm 302, which results in an L shape. In FIG. 19, the tool 300 has a ring 320 at the end of the arm 302, which results in a looped shape. In FIG. 20, the tool 300 has an arcuate segment 322, which results in a hook shape. The toll 300 may optionally have a consistent and/or constant cross-sectional shape or thickness. For example, in the illustrated embodiments, the tool 300 has a circular cross-section of essentially constant diameter. Such an embodiment may be advantageous in embodiments where increased rigidity is desired and/or where relatively equal rigidity/flexibility is desired in all directions (e.g., the flattened nature of the arms 116a and 116b may result in these structures exhibiting increased flexibility in certain directions only). Those of skill in the art will recognize any number of other shapes, sizes, and dimensions for the tool 300 that may be implemented.

Those of skill in the art will appreciate that the deployment system 100 can include the mesh prosthesis 106 having a non-inflammatory, bioabsorbable, biological oil coating composition to prevent tissue adhesion as is described in U.S. Pat. App. Pub. No. 2006/0078586, to support and deliver a therapeutic as described in U.S. Pat. No. 8,124,127, and/or to coat the mesh prosthesis 106 as described in US Pat. App. Pub. No. 2009/0181937 and U.S. Patent App. Pub. No. 2009/0208552, which are incorporated herein by reference in their entirety.

Such non-inflammatory, bioabsorbable, biological oil coating compositions can comprise a hydrophobic non-polymeric cross-linked gel, a fatty acid, and can optionally include one or more therapeutic agents. The coating can comprise the hydrophobic non-polymeric cross-linked gel and one or more fatty acids, and further comprise one or more of the group consisting of a glyceride, a glycerol, a fatty acid, and a fatty alcohol, and as mentioned previously also may further comprise a therapeutic agent.

The coating can be provided on all, or portions of, the mesh prosthesis 106 as would be appreciated by those of skill in the art. Further, the coating material can comprise both soluble and insoluble components. As used in the context of the cross-linked gel coating described herein, the terms "soluble" and "insoluble" refer the solubility of the coating in a polar solvent such as, e.g., tetrahydrofuran (THF), e.g., as determined by gravimetric analysis. For example, the coatings may be about 60%-75% soluble in THF and about 25%-40% insoluble in THF, or alternatively, the coatings may be about 45-55% soluble in THF and about 45-55% insoluble in THF, or alternatively, the coatings may be about 30%-55% soluble in THF and 45%-70% insoluble in THF, as determined by gravimetric analysis. Generally, at least some of the components resistant to extraction in organic solvent (such as THF) may include cross linked components, which may comprise free or esterified fatty acids with chain lengths of about $C_{10}$-$C_{22}$.

It should be noted that the term cross-linked gel, as utilized herein with reference to the present invention, refers to a gel that is non-polymeric and is derived from an oil composition comprising one or more fatty acids such as alpha-linolenic acid (ALA), eicosapentaenoic acid (EPA), and/or docosahexaenoic (DHA) covalently cross-linked directly to each other into a three-dimensional network by one or more of ester, lactone, ether, peroxide, and carbon-carbon bonds in a substantially random configuration. In various embodiments, the oil composition comprises a fatty acid molecule, a glyceride, and combinations thereof, any one or more of which may be cross-linked to each other into a three-dimensional network by one or more of ester, lactone, ether, peroxide, and carbon-carbon bonds in a substantially random configuration. In one embodiment, the bonds comprise hydrolysable bonds (e.g., ester and/or lactone cross-linking bonds). In one embodiment, the bonds comprise hydrolysable ester bonds. In one embodiment, the bonds comprise hydrolysable lactone ester bonds. In various embodiments the fatty acids are cross-linked to themselves via ester bonds.

In addition, the hydrophobic non-polymeric cross-linked gel coatings are bioabsorbable as described herein.

The hydrophobic non-polymeric cross-linked gel coatings can include a therapeutic agent as an active agent as contained in the coating and/or a prodrug that, e.g., becomes active once released from the coating. The coating may be selected such that it delivers or releases the therapeutic agent at a desired rate and/or therapeutically effective rate in vivo. In another embodiment, the coating may have an average drug loading of about 1-50% by weight.

The hydrophobic non-polymeric cross-linked gel coatings suitable for use on the surgical mesh 106 of the present invention are formed from an oil component. The term "oil component" is also referred to herein as the "oil-containing starting material." The "oil-containing starting material" may be natural or derived from synthetic sources. Preferably, the "oil containing starting material" comprises unsaturated fatty acids(e.g., unsaturated fish oil fatty acids, such as EPA, DHA and/or ALA). The oil component can be either an oil, or an oil composition. The oil component can be a naturally occurring oil, such as fish oil, cod liver oil, cranberry oil, a synthetic oil, or other oils having desired characteristics. One example embodiment makes use of a fish oil in part because of the high content of omega-3 fatty acids, which can provide healing support for damaged tissue, as discussed herein. The fish oil can also serve as an anti-adhesion agent. In addition, the fish oil maintains anti-inflammatory or non-inflammatory properties as well.

It should be noted that as utilized herein, the term "fish oil" includes but is not limited to omega-3 fatty acids, fish oil fatty acids, free fatty acids, monoglycerides, diglycerides, or triglycerides, esters of fatty acids, or a combination thereof. The fish oil may include one or more of arachidic acid, gadoleic acid, arachidonic acid, alpha-linoleic acid (ALA), eicosapentaenoic acid (EPA), docosahexaenoic acid (DHA), or derivatives, analogs and pharmaceutically acceptable salts thereof. Exemplary suitable derivatives include, but are not limited to, omega-3 fatty acid alkyl esters (e.g., omega-3 fatty acid ethyl esters). Other suitable derivatives would be apparent to the skilled artisan.

Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The naturally occurring oils, including fish oil, are cured as described herein to form a hydrophobic cross-linked gel, creating the coating.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance can be soluble in the phospholipid bi-layer of cells of body tissue, and therefore impact how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes. Biodegradable substances can cause inflammatory response due to either the parent substance or those formed during breakdown, and they may or may not be absorbed by tissues. Some biodegradable substances are limited to bulk erosion mechanism for breakdown.

The present invention contemplates the use of any commercially available surgical mesh 106 which is capable of being deployed with the resilient deployment structure 110 as described herein.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A medical device comprising:
   a mesh prosthesis having:
      a first layer of mesh affixed to a second layer of mesh proximate to a perimeter area thereof;
      an enclosure defined between the first layer of mesh and the second layer of mesh and extending inwardly from the perimeter area of the mesh prosthesis;
      an opening in the first layer of mesh passing through the first layer of mesh to the enclosure; and
      a fixation guide template defining a plurality of guide pockets within the enclosure;
   a resilient deployment structure removably disposed within the enclosure and extending toward the perimeter area, the resilient deployment structure having an elasticity that generates a resilient deployment force for urging the mesh prosthesis to a deployed configuration from a non-deployed configuration; and
   a plurality of shield projections spaced from each other about a perimeter of the deployment structure and extending outwardly from the perimeter of the deployment structure, wherein each of the shield projections is engaged within a corresponding one of the guide pockets to prevent relative rotational movement between the resilient deployment structure and the mesh prosthesis.

2. A system including the medical device of claim 1 and a fixation tool, wherein the shield projection forms a protective barrier for the second mesh layer from the fixation tool when the fixation tool is inserted into the enclosure during a fixation process in which the fixation tool affixes the first layer of mesh to tissue of a patient.

3. The system of claim 2, wherein the fixation tool is a tacker gun.

4. The system of claim 1, wherein the resilient deployment structure further comprises a separation line disposed in the resilient deployment structure extending in a generally serpentine shape from a central portion of the resilient deployment structure to the perimeter of the resilient deployment structure.

5. The system of claim 4, wherein the separation line comprises one or more through-holes.

6. The system of claim 4, wherein the separation line comprises a continuous groove at least partially cut into the resilient deployment structure.

7. The system of claim 4, further comprising a through-cut disposed at an end of the separation line.

8. The system of claim 4, further comprising a first arm arranged as a positioning tool for the medical device and a second arm arranged as a removal tool for the resilient deployment structure, such that a pulling force applied to the first arm initiates separation along the separation line, and the same pulling force applied to the second arm does not initiate separation along the separation line.

9. The system of claim 4, further comprising a first arm and a second arm of a handle assembly adapted to assume a locked configuration defining the handle assembly as a positioning tool for the medical device and an unlocked configuration defining the handle assembly as a removal tool for the resilient deployment structure.

10. The system of claim 9, wherein when the handle assembly is in the unlocked configuration, a pulling force applied to the first arm initiates separation along the separation line, and wherein the second arm is configured and positioned in such a way that the same pulling force applied to the second arm does not initiate separation along the separation line.

11. The system of claim 4, wherein separation along the separation line terminates at a ring formed by the perimeter of the resilient deployment structure.

12. The system of claim 1, further comprising a tool coupled to the resilient deployment structure and configurable as both a positioning tool and a deployment structure removal tool.

13. The system of claim 1, wherein the plurality of shield projections are positioned at equal interval distances from one another about the perimeter of the resilient deployment structure.

14. The system of claim 1, wherein the shield projections have a generally rectangular shape.

15. The system of claim 1, wherein the guide pockets have a generally rectangular shape.

16. The system of claim 1, wherein the guide pockets are defined by a plurality of walls formed by affixing the first layer of mesh to the second layer of mesh.

17. The system of claim 16, wherein the plurality of walls are formed by stitches, welds, adhesive, or combinations thereof, which couple the first layer of mesh to the second layer of mesh.

18. The system of claim 1, further comprising a coating material disposed on the mesh prosthesis.

19. The system of claim 18, wherein the coating material comprises a bio-absorbable cross-linked material having omega-3 fatty acids cross-linked into a substantially random configuration by ester bonds.

20. A mesh prosthesis, comprising:
a first layer of mesh fixed to a second layer of mesh formed along a perimeter area thereof in such a way that an enclosure extending from a central area of the mesh prosthesis to the perimeter area of the mesh prosthesis is formed between the first layer of mesh and the second layer of mesh;
an opening formed in the first layer of mesh and passing therethrough to the enclosure; and
a fixation guide template forming part of the enclosure, wherein the fixation guide template comprises a plurality of guide pockets formed by the first layer of mesh being fixed to the second layer of mesh at a fixation line, each of the guide pockets extending outwardly from the fixation line and placed at predetermined fixation intervals that are spaced apart from each other about the perimeter area.

* * * * *